(12) United States Patent
Androphy et al.

(10) Patent No.: US 10,420,753 B2
(45) Date of Patent: *Sep. 24, 2019

(54) COMBINATION THERAPIES FOR TREATMENT OF SPINAL MUSCULAR ATROPHY

(71) Applicants: Indiana University Research and Technology Corporation, Indianapolis, IN (US); The Brigham and Women's Hospital, Inc., Boston, MA (US)

(72) Inventors: Elliot J. Androphy, Indianapolis, IN (US); Kevin Hodgetts, Framingham, MA (US); Alyssa Nicole Calder, Cambridge, MA (US)

(73) Assignee: Indiana University Research and Technology Corporation, Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/862,751

(22) Filed: Jan. 5, 2018

(65) Prior Publication Data

US 2018/0235943 A1 Aug. 23, 2018

Related U.S. Application Data

(63) Continuation of application No. 15/440,727, filed on Feb. 23, 2017, now Pat. No. 9,895,358.

(60) Provisional application No. 62/351,773, filed on Jun. 17, 2016, provisional application No. 62/298,689, filed on Feb. 23, 2016.

(51) Int. Cl.

| | | |
|---|---|---|
| A61K 31/501 | (2006.01) | |
| A61K 31/50 | (2006.01) | |
| A61K 31/437 | (2006.01) | |
| A61K 31/444 | (2006.01) | |
| A61K 31/4704 | (2006.01) | |
| A61K 31/506 | (2006.01) | |
| A61K 45/06 | (2006.01) | |
| A61K 31/422 | (2006.01) | |
| A61K 31/426 | (2006.01) | |
| A61K 31/427 | (2006.01) | |
| A61K 31/4418 | (2006.01) | |
| A61K 31/4709 | (2006.01) | |
| A61K 31/4985 | (2006.01) | |
| A61K 31/517 | (2006.01) | |
| A61K 31/7125 | (2006.01) | |

(52) U.S. Cl.
CPC .......... *A61K 31/437* (2013.01); *A61K 31/422* (2013.01); *A61K 31/426* (2013.01); *A61K 31/427* (2013.01); *A61K 31/444* (2013.01); *A61K 31/4418* (2013.01); *A61K 31/4704* (2013.01); *A61K 31/4709* (2013.01); *A61K 31/4985* (2013.01); *A61K 31/501* (2013.01); *A61K 31/506* (2013.01); *A61K 31/517* (2013.01); *A61K 31/7125* (2013.01); *A61K 45/06* (2013.01); *A01K 2227/105* (2013.01); *A01K 2267/0318* (2013.01)

(58) Field of Classification Search
CPC ................ A61K 31/437; A61K 31/444; A61K 31/4704; A61K 31/501; A61K 31/506
See application file for complete search history.

(56) References Cited

U.S. PATENT DOCUMENTS

| | | | |
|---|---|---|---|
| 7,211,596 B2 | 5/2007 | Yoshida et al. | |
| 7,465,738 B2 | 12/2008 | Jarecki et al. | |
| 7,659,401 B2 | 2/2010 | Jaeschke et al. | |
| 7,879,848 B2 | 2/2011 | Lee et al. | |
| 8,343,997 B2 | 1/2013 | Oalmann et al. | |
| 8,658,650 B2 | 2/2014 | Conn et al. | |
| 8,895,592 B2 | 11/2014 | Frost et al. | |

FOREIGN PATENT DOCUMENTS

| | | | |
|---|---|---|---|
| EP | 1000946 A2 | 6/2000 | |
| JP | 2011160897 A | 8/2011 | |
| WO | 2006053120 A1 | 5/2006 | |
| WO | 2014012050 A2 | 1/2014 | |
| WO | 2014028459 A1 | 2/2014 | |
| WO | WO-2015118026 A1 * | 8/2015 | ........... A61K 31/428 |

OTHER PUBLICATIONS

Berge, et al., Pharmaceutical salts. J. Pharm. Sci., 1977, vol. 66, No. 1, pp. 1-19.
Calder et al., Small Molecules in Development for the Treatment of Spinal Muscular Atrophy. J. Med. Chem., 2016, 59(22), pp. 10067-10083.
Cifuentes-Diaz, et al., Neurofilament accumulation at the motor endplate and lack of axonal sprouting in a spinal muscular atrophy mouse model. Hum. Mol. Genet., 2000, vol. 11, No. 12, pp. 1439-1447.
Chan, et al., Neuromuscular defects in a *Drosophila* survival motor meuron gene mutant. Hum. Mol. Genet, 2003, vol. 12, No. 12, pp. 1367-1376.
Frugier, et al., Nuclear targeting defect of SMN lacking the C-terminus in a mouse model of spinal muscular atrophy, Hum Mol. Genet, 2000, vol. 9, No. 5, pp. 849-858.
Hsieh-Li, et al., A mouse model for spinal muscular atrophy. Nal Genet, 2000, vol. 24, No. 1, pp. 66-70.
Jablonka et al., Reduced survival motor neuron (Smn) gene dose in mice leads to motor neuron degeneration: an animal model for spinal muscular atrophy type III. Hum. Mol. Genet., 2000, vol. 9, No. 3, pp. 341-346.

(Continued)

*Primary Examiner* — Jean P Cornet
(74) *Attorney, Agent, or Firm* — Stinson LLP

(57) ABSTRACT

Disclosed herein are compositions and methods for treatment of spinal muscular atrophy (SMA). In certain embodiments, compounds are provided that increase full-length survival of motor neuron (SMN) protein production by an SMN2 gene.

18 Claims, 12 Drawing Sheets

(56) References Cited

OTHER PUBLICATIONS

McWhorter et al., Knockdown of the survival motor neuron (Smn) protein in zebrafish causes defects in motor axon outgrowth and pathfinding. J. Cell Biol., 2003, vol. 162, No. 5, pp. 919-931.

Meister, et al., SMN-mediated assembly of RNPs: a complex story. Trends Cell Biol., 2000, vol. 12, No. 10, pp. 472-478.

Monani, et al., The human centromeric survival motor neuron gene (SMN2) rescues embryonic lethality n Smn(−/−) mice and results in a mouse with spinal muscular atrophy. Hum Mol. Genet, 2000, vol. 9, No. 3, pp. 333-339.

Pellizzoni et al., Essential role for the SMN complex in the specificity of snRNP assembly. Science, 2002, vol. 298, No. 5599, pp. 1775-1779.

Rossoll, et al., Smn, the spinal muscular atrophy-determining gene product, modulates axon growth and localization of β-actin mRNA in growth cones of motoneurons. The Journal of Cell Biology, 2003, vol. 163, No. 4, pp. 801-812.

Cherry et al., Enhancement of SMN protein levels in a mouse model of spinal muscular atrophy using novel drug like compounds, EMBO Molecular Medicine, 2013, vol. 5, pp. 1035-1050.

Passini et al., CNS-targeted gene therapy improves survival and motor function in a mouse model of spinal muscular atrophy, The Journal of Clinical Investigation, vol. 120, No. 4, Apr. 2010, pp. 1253-1264.

Nevo et al., Spinal muscular atrophy, A preliminary result toward new therapy, American Academy of Neurology, 2016, vol. 86, pp. 884-885.

PubChem CID 87563722, Open Chemistry database, National Center for Biotechnology Information, Schembl 15093653, pp. 1-12, http:/lpubchem.ncbi.nlm_nih.gov/compound/86689638#section=1.

PubChem CID 86689638, Open Chemistry database, National Center for Biotechnology Information, SCHEMBL3718205, pp. 1-11, https:I/pubchem.ncbi.nlm.nih.gov/compound/87563722#section=1.

\* cited by examiner

Brain lysate: subcutaneous injection daily for 5 days, starting PND2, Harvest PND7
Formulation: PEG:PBS (50:50)
FVB is non-transgenic control mouse Brain lysate: PO daily for 5 days, starting PND2, Harvest PND7
Formulation: PEG:PBS (50:50)
FVB is non-transgenic control mouse

COMBINATION THERAPIES FOR TREATMENT OF SPINAL MUSCULAR ATROPHY

CROSS REFERENCE TO RELATED APPLICATIONS

This application is a continuation application of U.S. application Ser. No. 15/440,727, published as U.S. Publication No. 2017/0239225, filed Feb. 23, 2017, which claims priority to U.S. Provisional Application No. 62/298,689 filed Feb. 23, 2016, and U.S. Provisional Application No. 62/351,773 filed Jun. 17, 2016, which are hereby incorporated by reference in their entireties.

STATEMENT OF GOVERNMENT SUPPORT

This invention was made with government support under HD064850, NS064349, NS088522 and NS095139 awarded by the National Institutes of Health. The government has certain rights in the invention.

FIELD OF DISCLOSURE

The present disclosure relates to pharmaceutically active compounds and combinations thereof useful for treating, or lessening the severity of, spinal muscular atrophy.

BACKGROUND OF DISCLOSURE

Spinal muscular atrophy (SMA) is a neurological disorder that results from loss of function of the anterior horn cells in the spinal cord, manifesting as progressive motor weakness, muscle wasting, and paralysis. SMA is caused by insufficient levels of the survival motor neuron (SMN) protein. The SMN locus on chromosome 5q13 contains two inverted copies of SMN called SMN1 and SMN2. Most cases of SMA harbor homozygous deletions of the SMN1 gene and retain at least one copy of SMN2. With a carrier rate of about 1 in 40, SMA is estimated to be the most frequent genetic cause of infant mortality.

SMN2 is a gene duplication of SMN1 with the same predicted amino acid coding capacity. The nucleotide sequences of SMN1 and SMN2 are nearly identical. A critical difference is a C to T transition at the +6 position in exon 7, which dramatically influences the splicing pattern in these genes. Greater than 90% of SMN1 transcripts include exon 7, while there is less than 15% exon 7 inclusion in SMN2 transcripts. This alternatively spliced product produces a truncated and unstable form of the SMN protein. Any increase in the inclusion of exon 7 in SMN2 transcripts would result in higher levels of full length SMN protein, particularly, just doubling the amount of full length SMN2 mRNA could be clinically significant. A treatment that increases the amount of full length SMN2 mRNA should result in increased levels of SMN protein. It is believed that candidate drugs for treating SMA should (i) significantly increase cellular levels of SMN protein expression from the SMN2 gene; (ii) give consistent plasma and brain exposure in mouse (and predicted for human); and (iii) be efficacious in SMA mouse models. Based on this premise, an in vivo screen that can detect increases in full-length exon 7 included SMN2 transcripts was developed.

Current therapeutic strategies for SMA are mostly centered on elevating full length (wild type) SMN protein levels, modulating splicing towards exon 7 inclusion, stabilizing the wild type protein, and to a lesser extent, on restoring muscle function in SMA by providing trophic support or by inhibiting skeletal muscle atrophy. The mechanism leading to motorneuron loss and to muscular atrophy still remains obscure, although the availability of animal models of the disease is rapidly increasing knowledge in this field (Frugier T, et al. (2000) Hum Mol. Genet. 9:849-58; Monani U R, et al. (2000) Hum Mol Genet 9:333-9; Hsieh-Li H M, et al. (2000) Nat Genet 24:66-70; Jablonka S, et al. (2000) Hum Mol. Genet. 9:341-6). Also the function of SMN protein is still partially unknown, and studies indicate that it can be involved in mRNA metabolism (Meister G, et al. (2002). Trends Cell Biol. 12:472-8; Pellizzoni L, et al. (2002). Science. 298: 1775-9), and probably in transport of proteins/mRNA to neuromuscular junctions (Ci-fuentes-Diaz C, et al. (2002) Hum Mol. Genet. 11: 1439-47; Chan Y B, et al. (2003) Hum Mol. Genet. 12:1367-76; McWhorter M L, et al. (2003) J. Cell Biol. 162:919-31; Rossoll W, et al. (2003) J. Cell Biol. 163:801-812).

Accordingly, there is a need for new drugs to treat spinal muscular atrophy. SMN reporters can be used as tools for identifying and characterizing protein factors and chemical compounds that increase levels of full-length SMN protein through mechanisms, including, for example, increased transcription of SMN2, increased inclusion of exon 7 in the SMN2 mRNA, increased stability of the SMN2 mRNA, and decreased degradation of the full-length SMN protein. Results from high throughput systems to identify compounds that increase SMN protein using this cell based SMN-luciferase reporter assay are described herein. As such, the present disclosure provides compounds, as well as combinations of these compounds, useful for treating or lessening the severity of spinal muscular atrophy. The present disclosure also provides methods of treating or lessening the severity of spinal muscular atrophy comprising administering to a patient susceptible to or having spinal muscular atrophy a compound or composition of the present disclosure.

BRIEF DESCRIPTION

The present disclosure is generally related to compounds, compositions including the compounds, alone or in combination with other drugs known for treatment of SMA, and methods for treatment of spinal muscular atrophy (SMA) utilizing the compounds and compositions. In certain embodiments, compounds, and pro-drugs thereof, are provided that increase full-length survival of motor neuron (SMN) protein production by an SMN2 gene.

Accordingly, in one aspect, the present disclosure is directed to a composition including a SMN protein stabilizer and a SMN2 transcription enhancer. In some embodiments, the SMN protein stabilizer is a compound having the formula of formula (I):

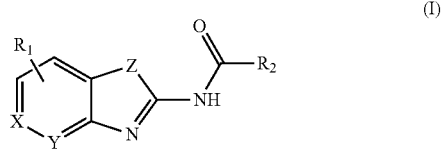

wherein X is selected from the group consisting of carbon or nitrogen;
Y is selected from the group consisting of carbon or nitrogen;

Z is selected from the group consisting of sulfur or oxygen;
R₁ is selected from hydrogen, alkyl, alkoxy, halogen, haloalky, and aminoalkyl; and
R₂ is selected from unsubstituted or substituted aryl and unsubstituted or substituted heteroaryl. In other embodiments, the SMN protein stabilizer is a compound having the formula of formula (III):

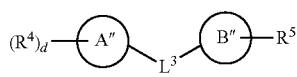
(III)

or a pharmaceutically acceptable salt thereof, wherein:

Ring A" is selected from an optionally substituted phenyl, a 5-6 membered monocyclic heteroaryl ring having 1-3 heteroatoms being nitrogen, or an 8-10 membered bicyclic heteroaryl ring having 1-4 heteroatoms independently selected from nitrogen, oxygen, or sulfur;

Ring B" is an optionally substituted 5-6 membered heteroaryl ring having 1-2 heteroatoms independently selected from nitrogen, oxygen, or sulfur;

L³ is —C(O)NH—;

each R⁴ is halogen or an optionally substituted $C_{1-6}$ aliphatic;

d is 0-5; and

R⁵ is $C_{1-6}$ linear or branched alkyl or a substituted $C_{3-6}$ cycloaliphatic, wherein the $C_{3-6}$ cycloaliphatic is substituted with at least one hydroxyl group. In yet other embodiments, the SMN protein stabilizer includes prodrugs of the compounds of formula (I) and (III).

The SMN2 transcription enhancer generally is a compound having the formula of formula (IV):

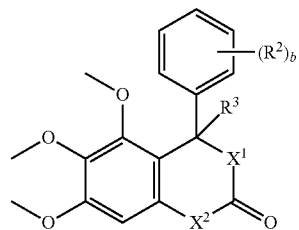
(IV)

or a pharmaceutically acceptable salt thereof, wherein
each of R² and R³ is independently halogen, R', —OR';
b is 1-5;
X¹ is —C(Rˣ)₂—, —NRˣ—, —NRˣC(Rˣ)₂— or —OC(Rˣ)₂—;
X² is —C(Rˣ)₂— or —NRˣ—;
each Rˣ is independently R', —(C₁₋₆ aliphatic)-N(R')₂, or —(C₁₋₆ aliphatic)-OR';
each R' is independently —R, —C(O)R, —CO₂R, or —SO₂R, or two R' on the same nitrogen are taken together with their intervening atoms to form a 3-7 membered heterocyclic ring having 1-2 heteroatoms independently selected from nitrogen, oxygen, and sulfur; and each R is hydrogen, or an optionally substituted group selected from C₁₋₆ aliphatic, phenyl, a 3-7 membered saturated or partially unsaturated carbocyclic ring, an 8-10 membered bicyclic saturated, partially unsaturated or aryl carbocyclic ring, a 5-6 membered monocyclic heteroaryl ring having 1-3 heteroatoms independently selected from nitrogen, oxygen, or sulfur, a 3-7 membered saturated or partially unsaturated heterocyclic ring having 1-2 heteroatoms independently selected from nitrogen, oxygen, or sulfur, an 8-10 membered bicyclic saturated or partially unsaturated heterocyclic ring having 1-4 heteroatoms independently selected from nitrogen, oxygen, or sulfur, or an 8-10 membered bicyclic heteroaryl ring having 1-4 heteroatoms independently selected from nitrogen, oxygen, or sulfur.

In another aspect, the present disclosure is directed to a method of treating spinal muscular atrophy in a subject in need thereof. The method includes administering the composition including a SMN protein stabilizer and a SMN2 transcription enhancer as set forth above.

In yet another aspect, the present disclosure is directed to a composition including a SMN2 splicing compound and a SMN2 transcription enhancer. The SMN2 transcription enhancer generally includes compounds having the formula (IV) as described above. In some embodiments, the SMN2 splicing compound is SMN-C2, having the formula:

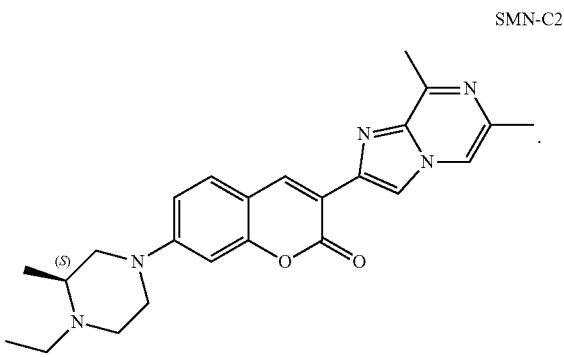
SMN-C2

In another embodiment, the SMN2 splicing compound is NVS-SM2, having the formula:

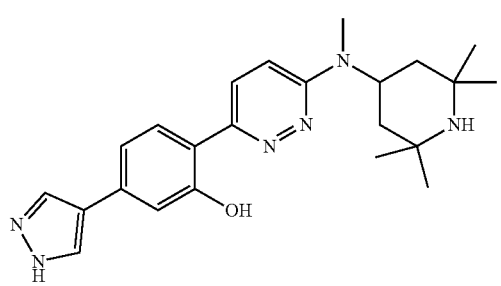
NVS-SM2

In yet another embodiment, the SMN2 splicing compound is nusinersen (all-P-ambo-2'-O—(2-methoxyethyl)-5-methyl-P-thiouridylyl-(3'→5')-2'-O-(2-methoxyethyl)-5-methyl-P-thiocytidylyl-(3'→5')-2'-O-(2-methoxyethyl)-P-thioadenylyl-(3'→5')-2'-O-(2-methoxyethyl)-5-methyl-P-thiocytidylyl-(3'→5')-2'-O-(2-methoxyethyl)-5-methyl-P-thiouridylyl-(3'→5')-2'-O-(2-methoxyethyl)-5-methyl-P-thiouridylyl-(3'→5')-2'-O-(2-methoxyethyl)-5-methyl-P-thiouridylyl-(3'→5')-2'-O-(2-methoxyethyl)-5-methyl-P-thiocytidylyl-(3'→5')-2'-O-(2-methoxyethyl)-P-thioadenylyl-(3'→5')-2'-O-(2-methoxyethyl)-5-methyl-P-thioadenylyl-(3'→5')-2'-O-(2-methoxyethyl)-P-thioadenylyl-(3'→5')-2'-O-(2-methoxyethyl)-P-thioadenylyl-(3'→5')-2'-O-(2-methoxyethyl)-5-methyl-P-thiouridylyl-(3'→5')-2'-O-(2-methoxyethyl)-P- thioguanylyl-(3'→5')-2'-O-(2-methoxyethyl)-5-methyl-P-thiocytidylyl-(3'→5')-2'-O-(2-methoxyethyl)-5-methyl-P-thiouridylyl-(3'→5')-2'-O-(2-methoxyethyl)-P-thioguanylyl-(3'→5')-2'-O-(2-methoxyethyl)guanosine), commercially available as SPINRAZA™.

In yet another aspect, the present disclosure is directed to a method of treating spinal muscular atrophy in a subject in need thereof. The method includes administering the composition including a SMN2 splicing compound and a SMN2 transcription enhancer as set forth herein.

In another aspect, the present disclosure is directed to a method of treating spinal muscular atrophy in a subject in need thereof. The method includes administering a SMN gene replacement therapy in combination with administering a composition comprising at least one of a SMN protein stabilizer and a SMN2 splicing compound. The SMN protein stabilizer generally includes compounds having the formula of formula (I) or (III), or prodrugs thereof as described above. The SMN2 transcription enhancer generally includes compounds having the formula (IV) as described above. The SMN gene replacement therapy can include the compound, AVXS-101.

DETAILED DESCRIPTION

1. Definitions

Figure 1A:
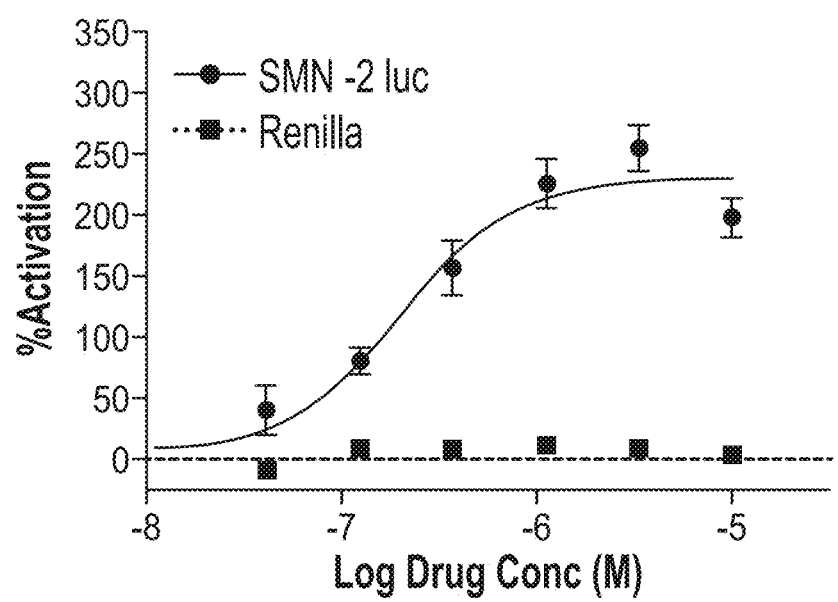
FIG. 1A is a graph depicting luciferase activity of Compound 291-88-1 (used interchangeably with Compound LDN-291-88-1).

Compounds of this disclosure include those described generally above, and are further illustrated by the embodiments, sub-embodiments, and species disclosed herein. As used herein, the following definitions shall apply to any one or more of the compounds described herein unless otherwise indicated. For purposes of this disclosure, the chemical elements are identified in accordance with the Periodic Table of the Elements, CAS version, Handbook of Chemistry and Physics, 75$^{th}$ Ed. Additionally, general principles of organic chemistry are described in "Organic Chemistry," Thomas Sorrell, University Science Books, Sausalito: 1999, and "March's Advanced Organic Chemistry," 5$^{th}$ Ed., Ed.: Smith, M. B. and March, J., John Wiley & Sons, New York: 2001, the entire contents of which are hereby incorporated by reference to the extent they are consistent herewith.

As described herein, compounds may optionally be substituted with one or more substituents, such as are illustrated generally above, or as exemplified by particular classes, subclasses, and species. It will be appreciated that the phrase "optionally substituted" is used interchangeably with the phrase "substituted or unsubstituted." In general, the term "substituted," whether preceded by the term "optionally" or not, refers to the replacement of hydrogen radicals in a given structure with the radical of a specified substituent. Unless otherwise indicated, an optionally substituted group may have a substituent at each substitutable position of the group, and when more than one position in any given structure may be substituted with more than one substituent selected from a specified group, the substituent may be either the same or different at every position. Combinations of substituents envisioned by this disclosure are preferably those that result in the formation of stable or chemically feasible compounds.

The term "stable," as used herein, refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

The term "heterocycle," "heterocyclyl," "heterocycloaliphatic," or "heterocyclic" as used herein means non-aromatic, monocyclic, bicyclic, or tricyclic ring systems in which one or more ring members is an independently selected heteroatom. In some embodiments, the "heterocycle," "heterocyclyl," "heterocycloaliphatic," or "heterocyclic" group has three to fourteen ring members in which one or more ring members is a heteroatom independently selected from oxygen, sulfur, nitrogen, or phosphorus, and each ring in the system contains 3 to 7 ring members.

A heterocyclic ring can be attached to its pendant group at any heteroatom or carbon atom that results in a stable structure and, when specified, any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl, and combinations thereof.

The term "heteroatom" refers to one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR+ (as in N-substituted pyrrolidinyl).

The term "unsaturated," as used herein, refers to a moiety having one or more units of unsaturation.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

The term "aryl" used alone or as part of a larger moiety as in "aralkyl," "aralkoxy," or "aryloxyalkyl," refers to monocyclic, bicyclic, and tricyclic ring systems having a total of five to fourteen ring members, wherein one or more ring in the system is aromatic and wherein each ring in the system contains 3 to 7 ring members. The term "aryl" may be used interchangeably with the term "aryl ring". The term "aryl" also refers to heteroaryl ring systems as defined herein below. In certain embodiments of the present disclosure, "aryl" refers to an aromatic ring system which includes, but not limited to, phenyl, biphenyl, naphthyl, anthracyl and the like and combinations thereof, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like and combinations thereof.

The term "heteroaryl," used alone or as part of a larger moiety as in "heteroaralkyl" or "heteroarylalkoxy," refers to monocyclic, bicyclic, and tricyclic ring systems having a total of five to fourteen ring members, wherein one or more ring in the system is aromatic, one or more ring in the system contains one or more heteroatoms, and wherein each ring in the system contains 3 to 7 ring members. The term "heteroaryl" may be used interchangeably with the term "heteroaryl ring" or the term "heteroaromatic". Heteroaryl groups include thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl and combinations thereof.

The terms "heteroaryl" and "heteroar-," as used herein, also include groups in which a heteroaromatic ring is fused to one or more aryl, cycloaliphatic, or heterocyclyl rings. Exemplary heteroaryl rings include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one and combinations thereof.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the disclosure.

Unless otherwise stated, all tautomeric forms of the compounds of the disclosure are within the scope of the disclosure.

Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{11}$C- or $^{13}$C- or $^{14}$C-enriched carbon are within the scope of this disclosure. Such compounds are useful, for example, as analytical tools or probes in biological assays.

2. General Description of Compounds of the Disclosure

The compounds of the present disclosure generally function to treat spinal muscular atrophy as SMN protein stabilizers. That is, "SMN protein stabilizer" refers to a compound or pro-drug thereof that acts by increasing the half-life of the SMN protein and decreasing its catabolism or turnover, allowing accumulation at higher levels in a cell. This could occur by interfering with its catabolism and degradation, for example, by the ubiquitin mediated proteasome pathway, or by autophagy, which are processes that mediate protein degradation.

According to one embodiment, the present disclosure provides a compound, or pro-drug thereof, of formula I:

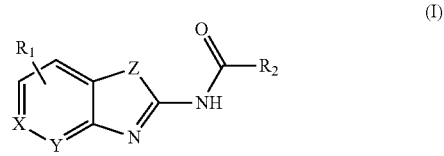

(I)

wherein X is selected from the group consisting of carbon or nitrogen;
Y is selected from the group consisting of carbon or nitrogen;
Z is selected from the group consisting of sulfur or oxygen;
$R_1$ is selected from hydrogen, alkyl, alkoxy, halogen, haloalky, and aminoalkyl; and $R_2$ is selected from unsubstituted or substituted aryl and unsubstituted or substituted heteroaryl. It has been found that the compounds of the present disclosure can treat, or lessen the severity of, spinal muscular atrophy by stabilizing SMN2. Such "SMN protein stabilizers" act by stabilizing the SMN2 mRNA and protein. Compounds of formula (1) are more fully described in WO 2014/012050 to Androphy et al., filed Jul. 12, 2013, which is hereby incorporated by reference to the extent it is consistent herewith.

According to one embodiment, the present disclosure provides a compound of formula II:

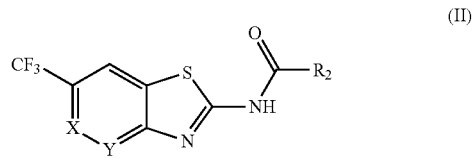

(II)

wherein X is selected from the group consisting of carbon or nitrogen;

Y is selected from the group consisting of carbon or nitrogen;

R₂ is selected from unsubstituted or substituted aryl, unsubstituted or substituted heteroaryl. In more particularly suitable embodiments, R₂ is selected from:

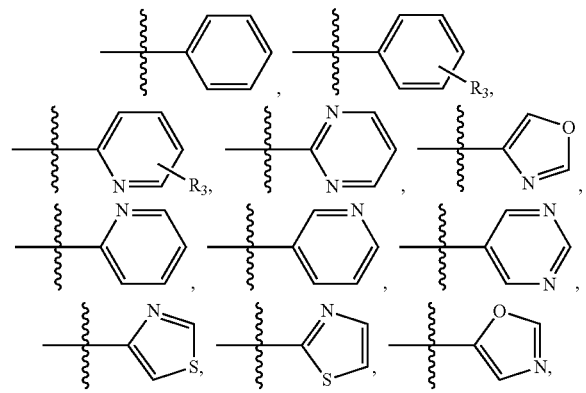

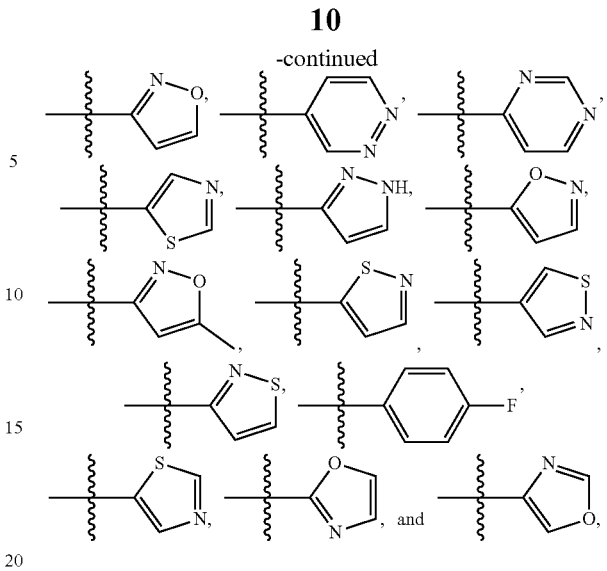

wherein $R_3$ is selected from alkyl, alkoxy, alkoxyalkyl, —O(CH₂)$_n$NR$^a$R$^b$, and halogen, and wherein n is an integer from 1-3 and R$^a$ and R$^b$ are independently selected from the group consisting of hydrogen and alkyl.

Exemplary compounds are set forth in Table 1 below.

TABLE 1

Exemplary Compounds

| Compound | Structure | EC50 (μM) | % Activation |
|---|---|---|---|
| 291-88-1 | 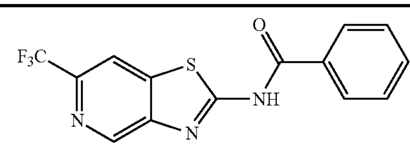 | 0.169 | 216 |
| 299-1-1 | 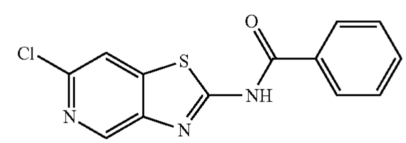 [SMILES: O=C(Nc1nc2cnc(Cl)cc2s1)c1ccccc1] | 2.02 | 154 |
| 299-15-1 | 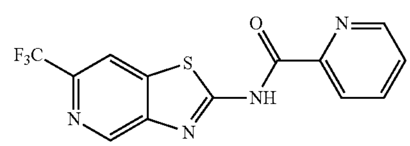 | 0.172 | 169.5 |
| 299-16-1 | 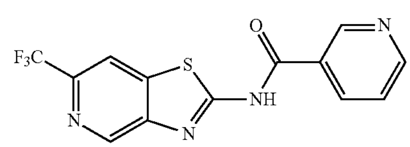 | 0.154 | 177 |
| 301-90-1 | 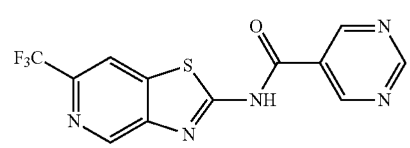 [SMILES: O=C(Nc1nc2cnc(C(F)(F)F)cc2s1)c1cncnc1] | 2.7 | 170 |
| 311-84 | 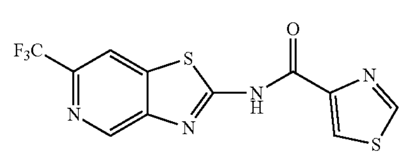 [SMILES: O=C(Nc1nc2cnc(C(F)(F)F)cc2s1)c1cscn1] | 0.62 | 270 |

TABLE 1-continued

Exemplary Compounds

| Compound | Structure | EC50 (μM) | % Activation |
|---|---|---|---|
| 311-65 | 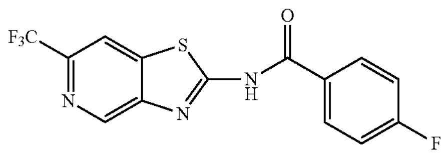 [SMILES: O=C(Nc1nc2cnc(C(F)(F)F)cc2s1)c1ccc(F)cc1] | 0.612 | 87.5 |
| 311-85 | 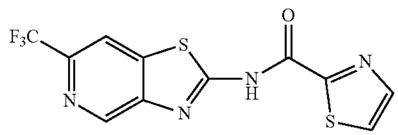 [SMILES: O=C(Nc1nc2cnc(C(F)(F)F)cc2s1)c1nccs1] | 0.163 | 218 |
| 299-53-1 | 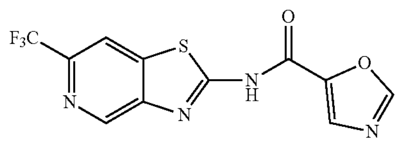 [SMILES: O=C(Nc1nc2cnc(C(F)(F)F)cc2s1)c1cnco1] | 4.4 | 200 |
| 299-54-1 | 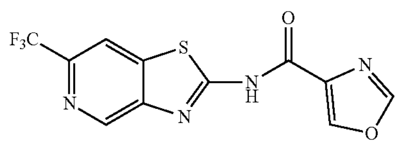 [SMILES: O=C(Nc1nc2cnc(C(F)(F)F)cc2s1)c1cocn1] | 1.135 | 208 |
| 299-55-1 | 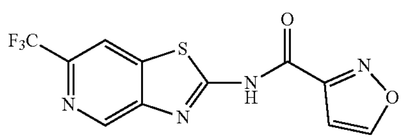 [SMILES: O=C(Nc1nc2cnc(C(F)(F)F)cc2s1)c1ccon1] | 0.245 | 245 |
| 299-63-1 | 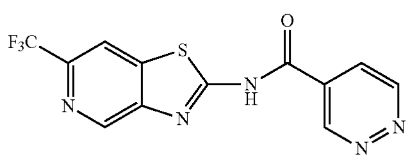 [SMILES: O=C(Nc1nc2cnc(C(F)(F)F)cc2s1)c1ccnnc1] | 11.3 | 163 |
| 299-73-1 | 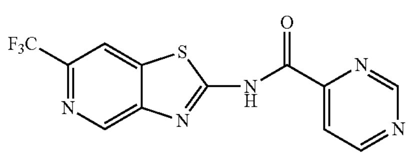 [SMILES: O=C(Nc1nc2cnc(C(F)(F)F)cc2s1)c1ccncn1] | 2.68 | 162 |
| 299-93-1 | 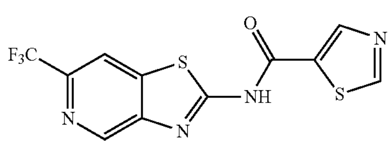 [SMILES: O=C(Nc1nc2cnc(C(F)(F)F)cc2s1)c1cncs1] | 0.142 | 140 |
| 324-2-1 | 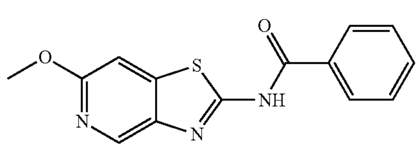 [SMILES: COc1cc2sc(NC(=O)c3ccccc3)nc2cn1] | 0.675 | 150 |
| 324-25-1 | 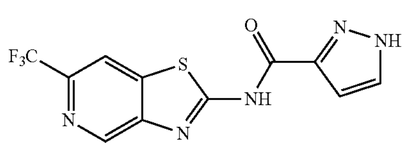 [SMILES: O=C(Nc1nc2cnc(C(F)(F)F)cc2s1)c1cc[nH]n1] | 2.04 | 178 |

TABLE 1-continued

Exemplary Compounds

| Compound | Structure | EC50 (μM) | % Activation |
|---|---|---|---|
| 324-26-1 | 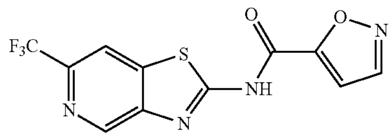 [SMILES: O=C(Nc1nc2cnc(C(F)(F)F)cc2s1)c1ccno1] | 0.214 | 193 |
| 324-33-1 | 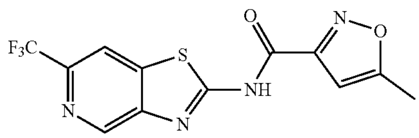 [SMILES: Cc1cc(C(=O)Nc2nc3cnc(C(F)(F)F)cc3s2)no1] | 5.4 | 110 |
| 324-36-1 | 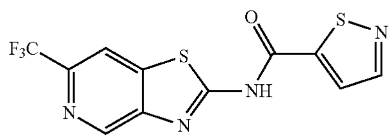 [SMILES: O=C(Nc1nc2cnc(C(F)(F)F)cc2s1)c1ccns1] | 0.064 | 198 |
| 324-44-1 | 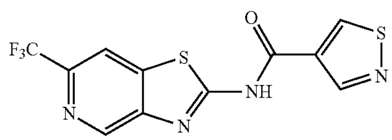 [SMILES: O=C(Nc1nc2cnc(C(F)(F)F)cc2s1)c1cnsc1] | 0.38 | 220 |
| 324-48-1 | 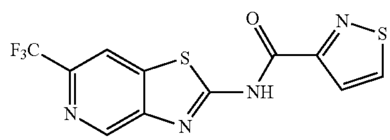 | 0.335 | 210 |
| 287-98-2 | 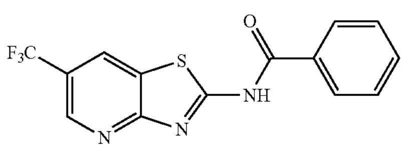 | 2.3 | 150 |
| 287-51-1 | 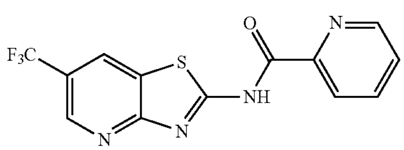 [SMILES: O=C(Nc1nc2ncc(C(F)(F)F)cc2s1)c1ccccn1] | 1 | 110 |
| 299-9-1 | 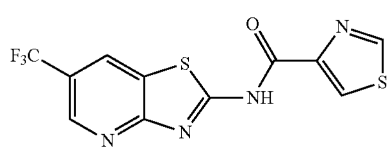 [SMILES: O=C(Nc1nc2ncc(C(F)(F)F)cc2s1)c1cscn1] | 1.22 | 154 |
| 299-10-1 | 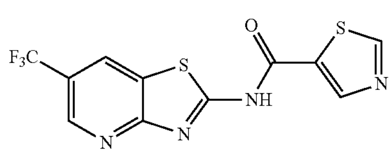 [SMILES: O=C(Nc1nc2ncc(C(F)(F)F)cc2s1)c1cncs1] | 3.2 | 112 |
| 301-62-1 | 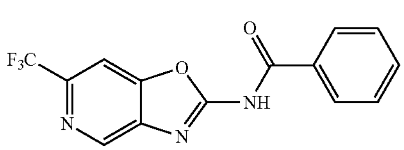 | 1.25 | 80 |

TABLE 1-continued

Exemplary Compounds

| Compound | Structure | EC50 (µM) | % Activation |
|---|---|---|---|
| N-(6-trifluoromethyl)thiazolo[4,5-c]pyridine-2-yl)oxazole-2-carboxamide | 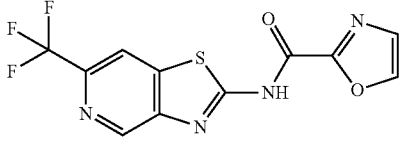 [SMILES: O=C(Nc1nc2cnc(C(F)(F)F)cc2s1)c1ncco1] | 1.3 | 74 |

It has been found that prodrugs of the above compounds can be used in the methods to provide improved pharmacokinetics and increase the levels of the above compounds in the subject. Exemplary pro-drugs of the compounds of formula (II) include for example, phosphono-oxymethylene pro-drugs of the compound 291-88-1, having the formulas selected from:

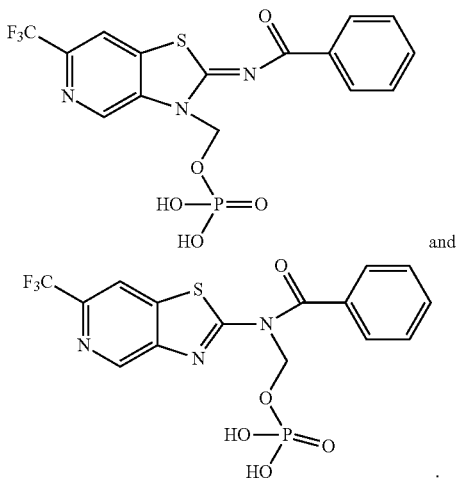

In some embodiments, the present disclosure provides a compound depicted in Table 1, above, or a pharmaceutically acceptable salt thereof.

3. General Methods of Providing the Above Compounds

The above compounds of this disclosure, including pro-drugs and salts thereof, may be prepared or isolated in general using known organic synthesis techniques and can be synthesized according to any of numerous possible synthetic routes.

Compounds of Formula (I) may be prepared, for example, according to the procedure shown in Scheme 1. Treatment of the required 4-halo-3-amino-pyridine with the appropriate isothiocyanate in acetone will form the desired compound.

Scheme 1

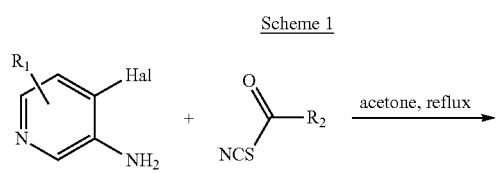

Alternatively, compounds of Formula (I) may be prepared according to the procedure shown in Scheme 2. Treatment of the appropriate aminothiazole and carboxylic acid with a suitable coupling agent (e.g., HATU, DCC, PyBOP, etc.) and an appropriate base (e.g., DIPEA, trimethylamine, etc.) will form the desired compound.

Scheme 2

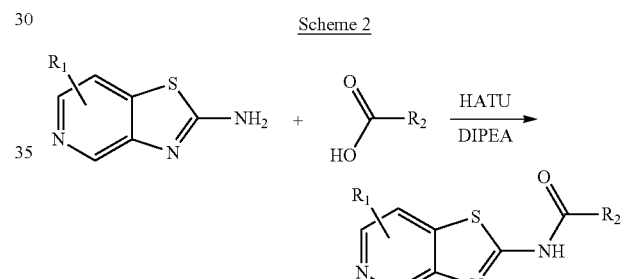

Additionally, compounds of Formula (I) may be prepared according to the procedure shown in Scheme 3. Treatment of the appropriate amino-pyridinol and di(1H-imidazol-1-yl)methanimine will give the desired aminooxazole and coupling with a suitable acid chloride will provide the desired compound.

Scheme 3

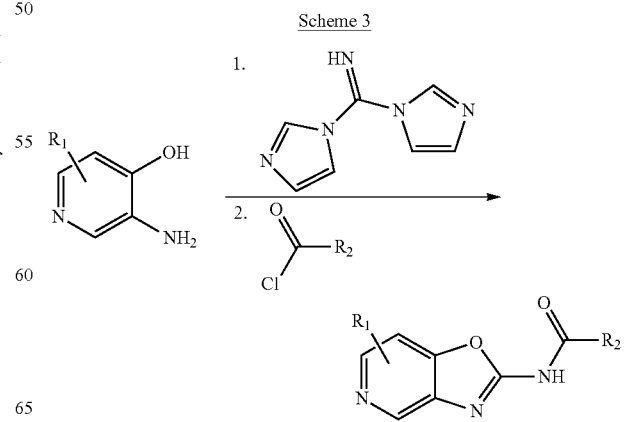

It will be appreciated by one skilled in the art that the processes described herein are not the exclusive means by which compounds provided herein may be synthesized, and that a broad repertoire of synthetic organic reactions is available to be potentially employed in synthesizing compounds of the present disclosure. One skilled in the art knows how to select and implement appropriate synthetic routes. Suitable synthetic methods of starting materials, intermediates and products may be identified by reference to the literature, including reference sources such as: Advances in Heterocyclic Chemistry, Vols. 1-107 (Elsevier, 1963-2012); Journal of Heterocyclic Chemistry Vols. 1-49 (Journal of Heterocyclic Chemistry, 1964-2012); Carreira, et al. (Ed.) Science of Synthesis, Vols. 1-48 (2001-2010) and Knowledge Updates KU2010/1-4; 2011/1-4; 2012/1-2 (Thieme, 2001-2012); Katritzky, et al. (Ed.) Comprehensive Organic Functional Group Transformations, (Pergamon Press, 1996); Katritzky et al. (Ed.); Comprehensive Organic Functional Group Transformations II (Elsevier, 2nd Edition, 2004); Katritzky et al. (Ed.), Comprehensive Heterocyclic Chemistry (Pergamon Press, 1984); Katritzky et al., Comprehensive Heterocyclic Chemistry II, (Pergamon Press, 1996); Smith et al., March's Advanced Organic Chemistry: Reactions, Mechanisms, and Structure, 6th Ed. (Wiley, 2007); Trost et al. (Ed.), Comprehensive Organic Synthesis (Pergamon Press, 1991).

The reactions for preparing compounds described herein can be carried out in suitable solvents, which can be readily selected by one of skill in the art of organic synthesis. Suitable solvents can be substantially non-reactive with the starting materials (reactants), the intermediates, or products at the temperatures at which the reactions are carried out, (e.g., temperatures that can range from the solvent's freezing temperature to the solvent's boiling temperature). A given reaction can be carried out in one solvent or a mixture of more than one solvent. Depending on the particular reaction step, suitable solvents for a particular reaction step can be selected by the skilled artisan.

Preparation of compounds described herein can involve the protection and deprotection of various chemical groups. The need for protection and deprotection, and the selection of appropriate protecting groups, can be readily determined by one skilled in the art. The chemistry of protecting groups can be found, for example, in T. W. Greene and P. G. M. Wuts, Protective Groups in Organic Synthesis, 3rd Ed., Wiley & Sons, Inc., New York (1999).

Reactions can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry, or by chromatographic methods such as high performance liquid chromatography (HPLC), liquid chromatography-mass spectroscopy (LCMS), or thin layer chromatography (TLC).

Compounds can be purified by those skilled in the art by a variety of methods, including high performance liquid chromatography (HPLC) and normal phase silica chromatography. Compounds can be characterized for identity and purity by any suitable technique, including nuclear magnetic resonance spectroscopy (e.g., $^1$H or $^{13}$C), infrared spectroscopy, mass spectrometry, or by chromatographic methods such as high performance liquid chromatography (HPLC), liquid chromatography-mass spectroscopy (LCMS).

The compounds provided by the present disclosure can be employed in combination therapies, meaning that the present compounds can be administered concurrently with, prior to, or subsequent to, one or more other desired therapeutic agents (e.g., known SMA therapeutic agent) or medical procedures. The particular combination of therapies (therapeutic agents or procedures) to employ in a combination regimen will take into account compatibility of the desired therapeutic agents and/or procedures and the desired therapeutic effect to be achieved. It will also be appreciated that the therapies employed may achieve a desired effect for the same disorder (for example, a compound described herein may be administered concurrently with another therapeutic agent used to treat the same disorder), or they may achieve different effects (e.g., control of any adverse effects).

For example, in one embodiment, one or more compounds described above are combined with a SMN2 transcription enhancer. As used herein, "SMN2 transcription enhancer" refers to a compound that acts by stimulating or increasing transcription of the SMN2 mRNA that encodes an SMN protein. Exemplary SMN2 transcription enhancers are prepared and identified as described in WO 2014/012050 to Androphy et al., filed Jul. 12, 2013, which is hereby incorporated by reference to the extent it is consistent herewith. More particularly, exemplary SMN2 transcription enhancers include those having the general formula of formula (IV):

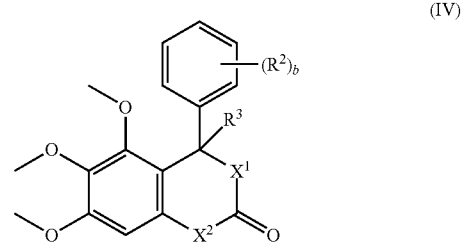

(IV)

or a pharmaceutically acceptable salt thereof, wherein
each of $R^2$ and $R^3$ is independently halogen, R', —OR';
b is 1-5;
$X^1$ is —C($R^x$)$_2$—, —N$R^x$—, —N$R^x$C($R^x$)$_2$— or —OC($R^x$)$_2$—;
$X^2$ is —C($R^x$)$_2$— or —N$R^x$—;
each $R^x$ is independently R', —(C$_{1-6}$ aliphatic)-N(R')$_2$, or —(C$_{1-6}$ aliphatic)-OR';
each R' is independently —R, —C(O)R, —CO$_2$R, or —SO$_2$R, or two R' on the same nitrogen are taken together with their intervening atoms to form a 3-7 membered heterocyclic ring having 1-2 heteroatoms independently selected from nitrogen, oxygen, and sulfur; and
each R is hydrogen, or an optionally substituted group selected from C$_{1-6}$ aliphatic, phenyl, a 3-7 membered saturated or partially unsaturated carbocyclic ring, an 8-10 membered bicyclic saturated, partially unsaturated or aryl carbocyclic ring, a 5-6 membered monocyclic heteroaryl ring having 1-3 heteroatoms independently selected from nitrogen, oxygen, or sulfur, a 3-7 membered saturated or partially unsaturated heterocyclic ring having 1-2 heteroatoms independently selected from nitrogen, oxygen, or sulfur, an 8-10 membered bicyclic saturated or partially unsaturated heterocyclic ring having 1-4 heteroatoms independently selected from nitrogen, oxygen, or sulfur, or an 8-10 membered bicyclic heteroaryl ring having 1-4 heteroatoms independently selected from nitrogen, oxygen, or sulfur.

More particularly, exemplary SMN2 transcription enhancers include those in Table 2:
TABLE 2
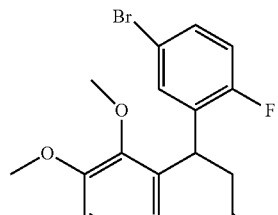
LDN-76070
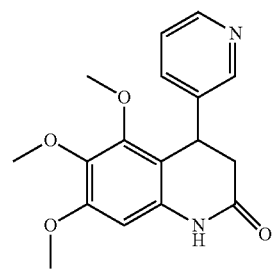 [SMILES: COc1cc2c(c(OC)c1OC)C(c1cccnc1)CC(=O)N2]
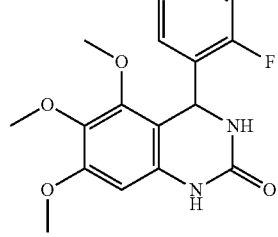
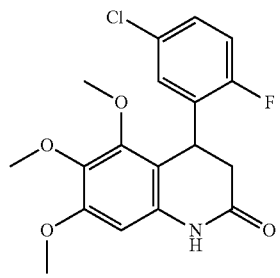 [SMILES: COc1cc2c(c(OC)c1OC)C(c1cc(Cl)ccc1F)CC(=O)N2]
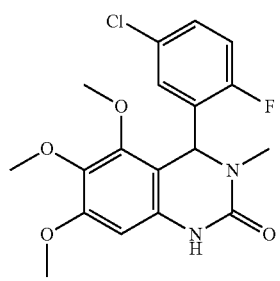
TABLE 2-continued
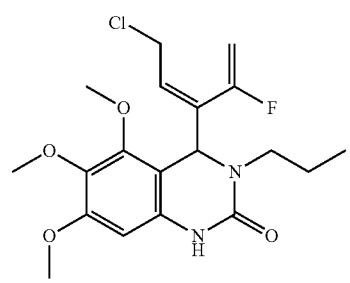 [SMILES: C=C(F)/C(=C\CCl)C1c2c(cc(OC)c(OC)c2OC)NC(=O)N1CCC]
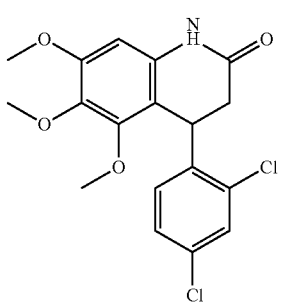 [SMILES: COc1cc2c(c(OC)c1OC)C(c1ccc(Cl)cc1Cl)CC(=O)N2]
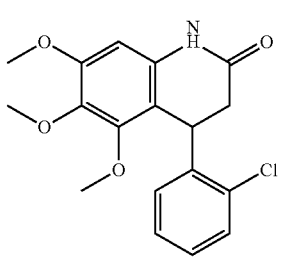 [SMILES: COc1cc2c(c(OC)c1OC)C(c1ccccc1Cl)CC(=O)N2]
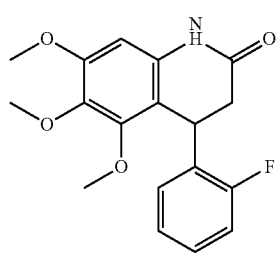 [SMILES: COc1cc2c(c(OC)c1OC)C(c1ccccc1F)CC(=O)N2]

TABLE 2-continued
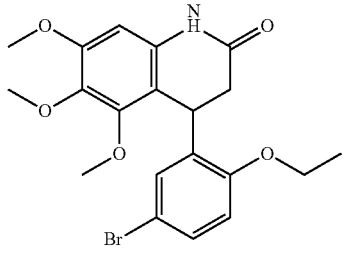 [SMILES: CCOc1ccc(Br)cc1C1CC(=O)Nc2cc(OC)c(OC)c(OC)c21]
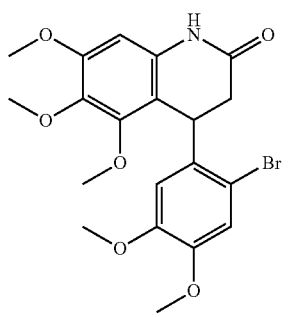 [SMILES: COc1cc(Br)c(C2CC(=O)Nc3cc(OC)c(OC)c(OC)c32)cc1OC]
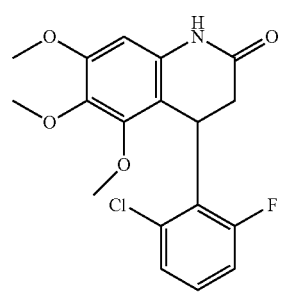 [SMILES: COc1cc2c(c(OC)c1OC)C(c1c(F)cccc1Cl)CC(=O)N2]
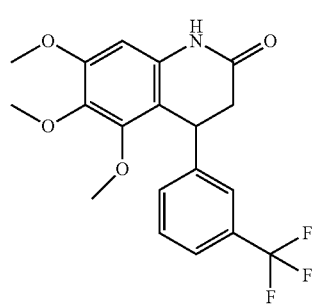 [SMILES: COc1cc2c(c(OC)c1OC)C(c1cccc(C(F)(F)F)c1)CC(=O)N2]
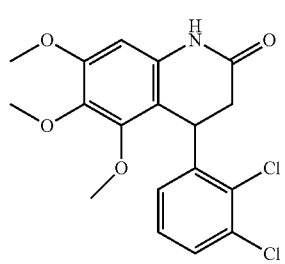 [SMILES: COc1cc2c(c(OC)c1OC)C(c1cccc(Cl)c1Cl)CC(=O)N2]
TABLE 2-continued
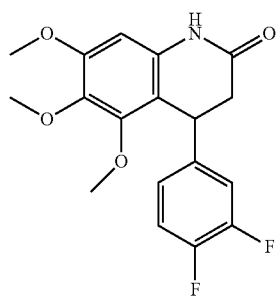 [SMILES: COc1cc2c(c(OC)c1OC)C(c1ccc(F)c(F)c1)CC(=O)N2]
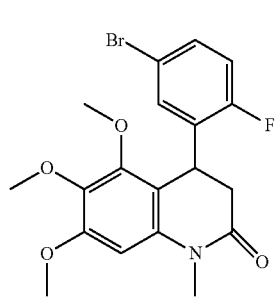 [SMILES: COc1cc2c(c(OC)c1OC)C(c1cc(Br)ccc1F)CC(=O)N2C]
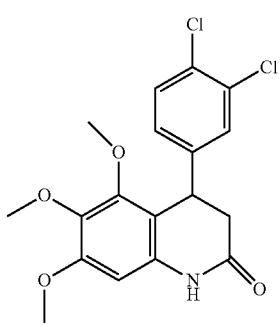 [SMILES: COc1cc2c(c(OC)c1OC)C(c1ccc(Cl)c(Cl)c1)CC(=O)N2]
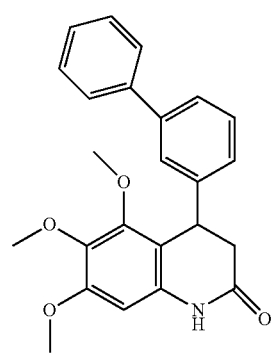 [SMILES: COc1cc2c(c(OC)c1OC)C(c1cccc(-c3ccccc3)c1)CC(=O)N2]
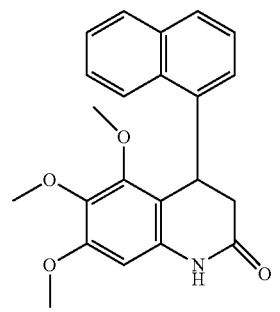 [SMILES: COc1cc2c(c(OC)c1OC)C(c1cccc3ccccc13)CC(=O)N2]

TABLE 2-continued

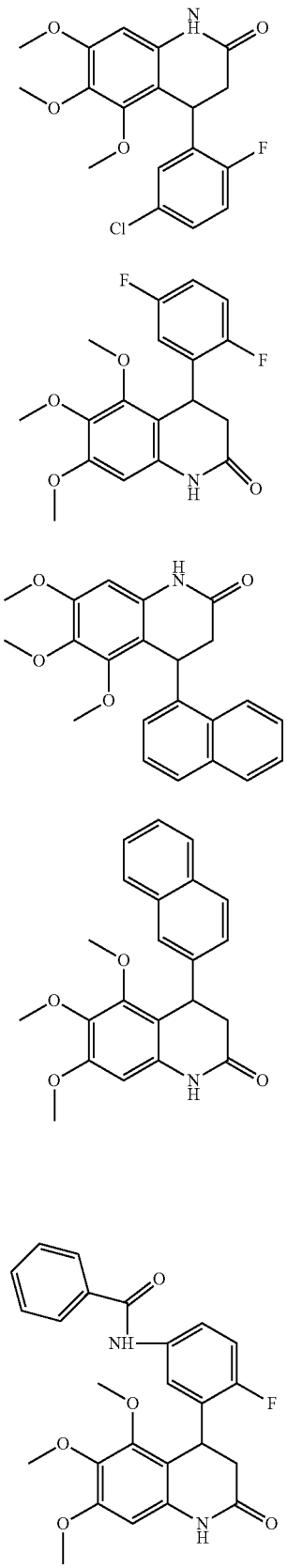

TABLE 2-continued

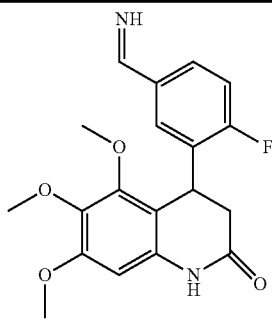

Yet further examples can be found in the Calder et al., J. Med. Chem., 2016, 59(22), pp. 10067-10083, which is incorporated by reference to the extent it is consistent herewith.

In yet another embodiment, the present disclosure provides compositions including one or more of the compounds described herein in combination with one or more compound that are known SMN2 splicing compounds. As used herein, "SMN2 splicing compound" refers to a compound that promotes catalyzing an excision reaction in a SMN2 pre-mRNA transcript resulting in an exon composition that includes exon 7. Exemplary SMN2 splicing compounds include:

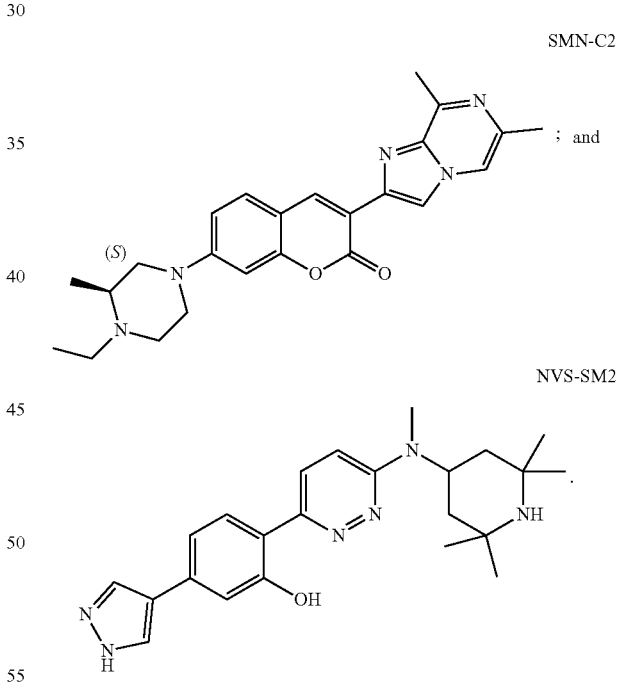

In yet another embodiment, the SMN2 splicing compound is nusinersen (all-P-ambo-2'-O— (2-methoxyethyl)-5-methyl-P-thiouridylyl-(3'→5')-2'-O-(2-methoxyethyl)-5-methyl-P-thiocytidylyl-(3'→5')-2'-O-(2-methoxyethyl)-P-thioadenylyl-(3'→5')-2'-O-(2-methoxyethyl)-5-methyl-P-thiocytidylyl-(3'→5')-2'-O-(2-methoxyethyl)-5-methyl-P-thiouridylyl-(3'→5')-2'-O-(2-methoxyethyl)-5-methyl-P-thiouridylyl-(3'→5')-2'-O-(2-methoxyethyl)-5-methyl-P-thiouridylyl-(3'→5')-2'-O-(2-methoxyethyl)-5-methyl-P-thiocytidylyl-(3'→5')-2'-O-(2-methoxyethyl)-P-thioadenylyl-(3'→5')-2'-O-(2-methoxyethyl)-5-methyl-P- thiouridylyl-(3'→5')-2'-O-(2-methoxyethyl)-P-thioadenylyl-(3'→5')-2'-O-(2-methoxyethyl)-P-thioadenylyl-(3'→5')-2'-O-(2-methoxyethyl)-5-methyl-P-thiouridylyl-(3'→5')-2'-O-(2-methoxyethyl)-P-thioguanylyl-(3'→5')-2'-O-(2-methoxyethyl)-5-methyl-P-thiocytidylyl-(3'→5')-2'-O-(2-methoxyethyl)-5-methyl-P-thiouridylyl-(3'→5')-2'-O-(2-methoxyethyl)-P-thioguanylyl-(3'→5')-2'-O-(2-methoxyethyl)guanosine), commercially available as SPINRAZA™. Yet further examples can be found in the Calder et al., J. Med. Chem., 2016, 59(22), pp. 10067-10083, which is incorporated by reference to the extent it is consistent herewith.

Alternatively, in some embodiments, compositions for treating SMA may include a SMN2 transcription enhancer and/or a SMN2 splicing compound as described above and further includes one more SMN protein stabilizer other than the compounds of formula (I) or (II) of the present disclosure. For example, in some embodiments, the compositions include SMN protein stabilizers prepared and identified as described in WO 2014/012050 to Androphy et al., filed Jul. 12, 2013, which is hereby incorporated by reference to the extent it is consistent herewith. More particularly, exemplary SMN2 protein stabilizers include those having the general formula of formula (III):

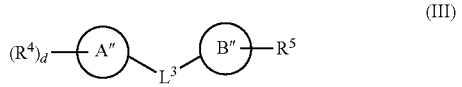

(III)

or a pharmaceutically acceptable salt thereof, wherein:
Ring A" is selected from an optionally substituted phenyl, a 5-6 membered monocyclic heteroaryl ring having 1-3 heteroatoms being nitrogen, or an 8-10 membered bicyclic heteroaryl ring having 1-4 heteroatoms independently selected from nitrogen, oxygen, or sulfur;
Ring B" is an optionally substituted 5-6 membered heteroaryl ring having 1-2 heteroatoms independently selected from nitrogen, oxygen, or sulfur;
$L^3$ is —C(O)NH—;
each $R^4$ is halogen or an optionally substituted $C_{1-6}$ aliphatic;
d is 0-5; and
$R^5$ is $C_{1-6}$ linear or branched alkyl or a substituted $C_{3-6}$ cycloaliphatic, wherein the $C_{3-6}$ cycloaliphatic is substituted with at least one hydroxyl group.

In particularly suitable embodiment, Ring B" is selected from the group consisting of:

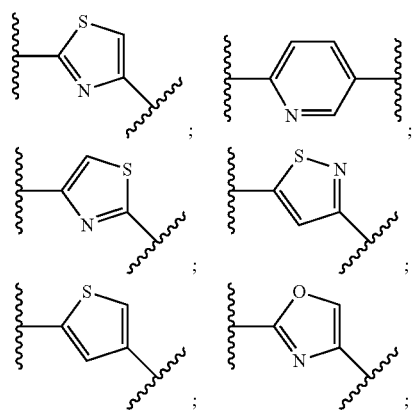

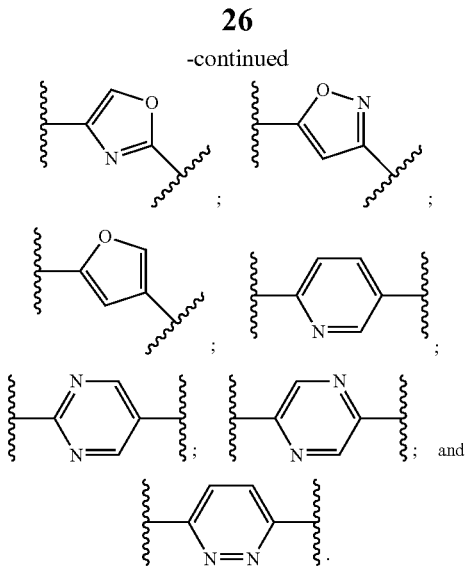

In one further particularly suitable embodiment, $R^5$ is a substituted $C_{3-4}$ cycloaliphatic, wherein the $C_{3-4}$ cycloaliphatic is substituted with at least one hydroxyl group. Exemplary compounds include those compounds described in WO 2014/012050, which is hereby incorporated by reference to the extent it is consistent herewith.

In some particularly preferred embodiments, the SMN2 protein stabilizers include those in Table 3:

TABLE 3

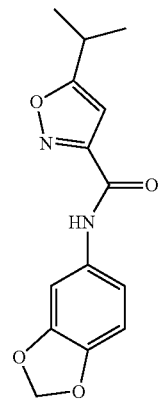 [SMILES: CC(C)c1cc(C(=O)Nc2ccc3c(c2)OCO3)no1]

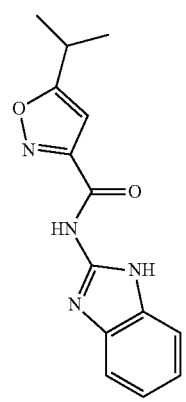 [SMILES: CC(C)c1cc(C(=O)Nc2nc3ccccc3[nH]2)no1]

TABLE 3-continued

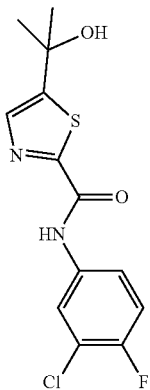 [SMILES: CC(C)(O)c1cnc(C(=O)Nc2ccc(F)c(Cl)c2)s1]
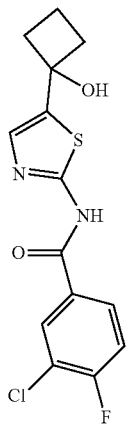 [SMILES: O=C(Nc1ncc(C2(O)CCC2)s1)c1ccc(F)c(Cl)c1]
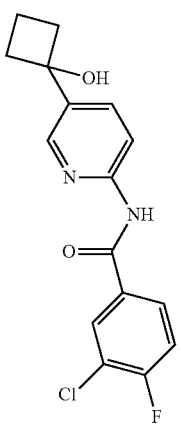 [SMILES: O=C(Nc1ccc(C2(O)CCC2)cn1)c1ccc(F)c(Cl)c1]
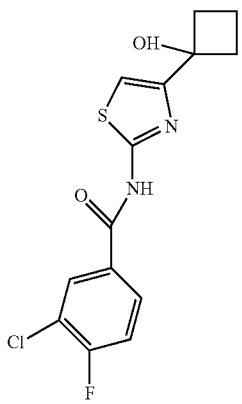 [SMILES: O=C(Nc1nc(C2(O)CCC2)cs1)c1ccc(F)c(Cl)c1]
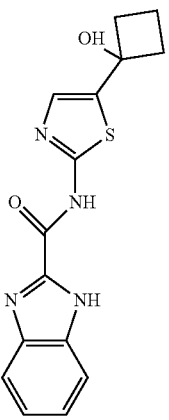 [SMILES: O=C(Nc1ncc(C2(O)CCC2)s1)c1nc2ccccc2[nH]1]
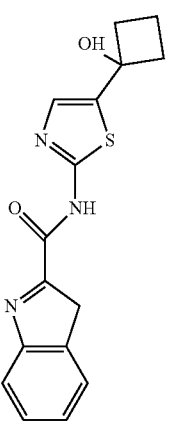 [SMILES: O=C(Nc1ncc(C2(O)CCC2)s1)C1=Nc2ccccc2C1]

In yet another embodiment, the compositions of the present disclosure include a SMN protein stabilizer and/or a SMN2 transcription enhancer in combination with a SMN gene replacement therapy. The SMN protein stabilizer generally includes compounds having the formula of formula (I) or (III), or prodrugs thereof, as described above. The SMN2 transcription enhancer generally includes compounds having the formula (IV) as described above. The SMN gene replacement therapy can include the compound, AVXS-101.

The amount of additional therapeutic agent present in the compositions of this disclosure will be no more than the amount that would normally be administered in a composition comprising that therapeutic agent as the only active agent. In certain embodiments, the amount of additional therapeutic agent in the present compositions will range from about 50% to 100% of the amount normally present in a composition comprising that agent as the only therapeutically active agent.

In an alternate embodiment, the methods of this disclosure utilize compositions that do not contain an additional therapeutic agent, comprise the additional step of separately administering to said patient an additional therapeutic agent. When these additional therapeutic agents are administered separately they may be administered to the patient prior to, sequentially with or following administration of the compositions of this disclosure.

4. Pharmaceutically Acceptable Compositions

It will be appreciated that certain of the compounds described herein can exist in free form for treatment, or where appropriate, as a pharmaceutically acceptable salt thereof.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. A "pharmaceutically acceptable salt" means any non-toxic salt or salt of an ester of a compound of this disclosure that, upon administration to a recipient, is capable of providing, either directly or indirectly, a compound of this disclosure or a pharmaceutically active metabolite or residue thereof. As used herein, the term "pharmaceutically active metabolite or residue thereof" means that a metabolite or residue thereof is also a pharmaceutically active compound in accordance with the present disclosure.

Pharmaceutically acceptable salts are well known in the art. For example, S. M. Berge et al., describes pharmaceutically acceptable salts in detail in *J. Pharmaceutical Sciences*, 1977, 66, 1-19, incorporated herein by reference to the extent it is consistent herewith. Pharmaceutically acceptable salts of the compounds of this disclosure include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+$ $(C_{1-4}$ alkyl$)_4$ salts. This disclosure also envisions the quaternization of any basic nitrogen-containing groups of the compounds disclosed herein. Water or oil-soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

In some cases, compounds of the present disclosure may contain one or more acidic functional groups and, thus, may be capable of forming pharmaceutically-acceptable salts with pharmaceutically-acceptable bases. The term "pharmaceutically-acceptable salts" in these instances refers to the relatively non-toxic, inorganic and organic base addition salts of compounds of the present disclosure. These salts can likewise be prepared in situ in the administration vehicle or the dosage form manufacturing process, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethyldiamine, ethanolamine, diethanolamine, piperazine and the like.

According to another aspect of the present disclosure, pharmaceutically acceptable compositions are provided, wherein these compositions comprise any of the compounds as described herein, and optionally comprise a pharmaceutically acceptable carrier, adjuvant or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired.

Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the disclosure, such as by producing any undesirable biological effect or otherwise interacting in a deleterious manner with any other component(s) of the pharmaceutically acceptable composition, its use is contemplated to be within the scope of this disclosure. Some examples of materials, which can serve as pharmaceutically acceptable carriers, include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethyl-polyoxypropyl-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propyl glycol or polyethyl glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. In some embodiments, the compositions of the present disclosure additionally comprise one or more of DMSO, PEG400, Tween-80, and hydropropyl beta cyclodextrin (HP-j-CD).

The pharmaceutically acceptable compositions of this disclosure can be administered to humans and other animals orally, rectally, parenterally, intravenously, subcutaneously, intracisternally, intravaginally, intraperitoneally, topically (as by powders, ointments, or drops), bucally, as an oral or nasal spray, or the like, or combinations thereof, depending on the severity of the disorder being treated.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propyl glycol, 1,3-butyl glycol, dimethylformamide, oils (in particular, cottonseed, groundnut, corn, germ, olive, castor, and sesame oils), glycerol, tetrahydrofurfuryl alcohol, polyethyl glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present disclosure, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this disclosure with suitable non-irritating excipients or carriers such as cocoa butter, polyethyl glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with one or more inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethyl glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethyl glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethyl glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms, the active compound may be admixed with one or more inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this disclosure include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this disclosure. Additionally, the present disclosure contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Uses of Compounds and Pharmaceutically Acceptable Compositions

The compounds of the disclosure are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present disclosure (also referred to herein as "therapeutically effective amount") will be decided by the attending physician within the scope of sound medical judgment. More particularly, as used herein, the phrase "therapeutically effective amount" of the compound used in the methods of the present disclosure refers to a sufficient amount of a compound to treat SMA as defined herein, at a reasonable benefit/risk ratio applicable to any medical treatment. It can be understood, however, that the total daily usage of the compound and pharmaceutically acceptable compositions including the compound for use in the methods of the present disclosure can be decided by the attending physician within the scope of sound medical judgment. The specific therapeutically effective dose level for any particular patient can depend upon a variety of factors including the loss of motor neuron function episode being treated and the severity of the episode; activity of the specific compound employed; the specific pharmaceutically acceptable composition employed; the age, body weight, general health, sex and diet of the patient; the time of administration, route of administration, and rate of excretion of the compound employed; the duration of the treatment; drugs used in combination or coincidental with the specific compound employed; and like factors well-known in the medical arts. For example, it is well within the skill of the art to start doses of the compound at levels lower than required to achieve the desired therapeutic effect and to gradually increase the dosage until the desired effect is achieved.

The terms "patient" and "subject" are used interchangeably herein, to refer to an animal, preferably a mammal, and most preferably a human. Particularly, the patient refers to a subject that is susceptible to or has SMA. As used herein, "susceptible to" refers to having little resistance to a certain disease, disorder or condition, and in particular, to SMA, including being genetically predisposed, having a family history of, and/or having symptoms of the disease, disorder or condition. Accordingly, in some embodiments, the compounds and/or pharmaceutically acceptable compositions can be administered to a subset of subjects in need of preventing/minimizing/controlling loss of motor neuron function, progressive motor weakness, muscle wasting, and paralysis. Some subjects that are in specific need of restored/maintained motor neuron function may include patients who are susceptible to, or at elevated risk of, experiencing loss of motor neuron function, including subjects susceptible to, or at elevated risk of, areflexia, muscle weakness, poor muscle tone, muscle wasting, paralysis, fasciculations of the tongue, difficulty sucking or swallowing, arthrogryposis, low weight, and the like. In one particular embodiment, the methods can be administered to a patient who has, or is susceptible to, or at elevated risk of, SMA. Subjects may be susceptible to, or at elevated risk of, experiencing SMA, and generally, loss of motor neuron function, muscle weakness, poor muscle tone, muscle wasting, paralysis, fasciculations of the tongue, difficulty sucking or swallowing, arthrogryposis, low weight due to family history, age, environment, and/or lifestyle. Based on the foregoing, because some of the method embodiments of the present disclosure are directed to specific subsets or subclasses of identified subjects (that is, the subset or subclass of patients susceptible to one or more specific conditions noted herein), not all subjects will fall within the subset or subclass of subjects as described herein for certain diseases, disorders or conditions.

Various functions and advantages of these and other embodiments of the present disclosure will be more fully understood from the examples described below. The following examples are intended to illustrate the benefits of the present disclosure, but do not exemplify the full scope of the disclosure.

EXAMPLES

Example 1

In this Example, compound 291-88-1 of the present disclosure was evaluated in vitro for SMN expression activity.

SMN2-Luciferase Reporter Assay

In this high throughput screening assay, the SMN promoter was combined with exons 1-6 and an exon 7 splicing cassette in a single construct that should respond to compounds that increase SMN transcription, exon 7 inclusion, or that might stabilize the SMN RNA or protein. A stable clonal HEK293 cell line that expresses the SMN2 reporter was isolated. Particularly, cells were incubated at 37° C. with 5% $CO_2$. HEK-293 cells were cultured in D-MEM (Gibco 11995) with 10% fetal bovine serum (FBS; Atlas) and 1× pen-strep (Gibco 15140). Reporter cell lines containing SMN1, SMN2, or SV40 driven firefly luciferase reporters and a control (renilla luciferase reporter) were selected and maintained in D-MEM with 10% FBS and 1× pen-strep with 200 μg/mL hygromycin B (Invitrogen 10687-010). 3813 and 3814 fibroblasts were cultured in D-MEM (Gibco 11995) with 10% fetal bovine serum (FBS; Atlas) and 1× pen-strep (Gibco 15140).

The HEK293 reporter cell lines were then plated at 50,000 cells per well in 96-well plates and incubated overnight. Compound 291-88-1 was added to each well and incubated at 37° C. overnight. The final DMSO concentration was 0.1%. Luciferase activity was assayed with either SteadyGlo (Promega E2510) or DualGlo (Promega E2920) luciferase using the Pherastar FS (BMG Labtech) plate reader. For detailed assay conditions, see Table 4. All data points were transformed from light units to percentage increase over basal expression in the treated control wells (DMSO concentration as appropriate, usually 0.1%) and expressed as percent activation (FIG. 1A).

TABLE 4

SMN-Luciferase Standard Conditions: 96-well Format

| Sequence | Parameter | Value | Description |
|---|---|---|---|
| 1 | Cells | 100 μL | 50,000 cells/well 96 TC-treated white plate |
| 2 | Time | 24 hours | 37° C. 5% $CO_2$ |
| 3 | Compound | 100 μL | With compound 2X concentration |
| 4 | Time | 24 hours | 37° C. 5% $CO_2$ |
| 5 | Remove media from wells | | |
| 6 | Reagent | 30 μL | SteadyGlo or DualGlo reagent (Promega) |
| 7 | Time | 30 seconds | Room temperature |

TABLE 4-continued

SMN-Luciferase Standard Conditions: 96-well Format

| Sequence | Parameter | Value | Description |
|---|---|---|---|
| 8 | Detector | 1.0 s integration | Pherastar FS |

Protein Detection

Figure 1B:
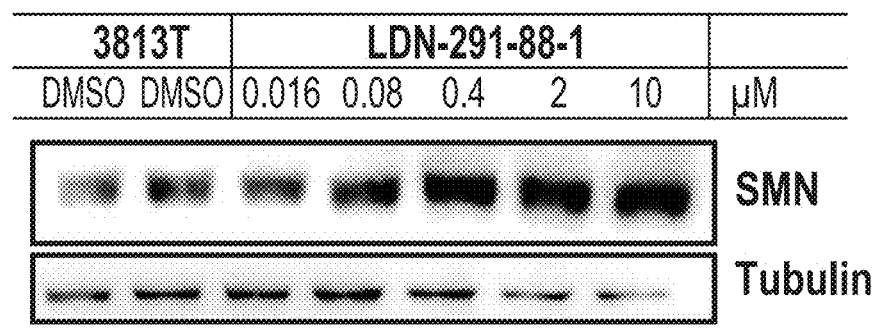
FIGS. 1B & 1C depict the effects of compound 291-88-1 on SMN protein expression in patient-derived fibroblasts (3813 cells; SMN1−/−SMN2+/+).
Figure 1C:
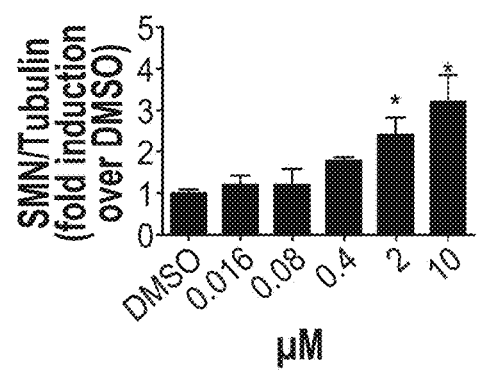

For detection of SMN protein in patient fibroblasts, 8000 cells per $cm^2$ were plated 24 hours prior to compound addition. Since SMN is expressed ubiquitously, cells containing even one copy of the human SMN1 gene will mask the effects of compounds on expression from the SMN2 gene. SMN null cells are not viable. The current standard is to use a human cell line derived from a severe SMA patient. The fibroblast strain 3813 is SMN1 null with three copies of SMN2. 3814 cells from the carrier parent (SMN1+/− with two copies of SMN2) express ~3-5 times more full-length SMN protein than 3813 cells (Coriel GM03813). hTERT immortalized 3813 and 3814 cell clones called 3813T and 3814T, respectively, were isolated to measure endogenous SMN protein levels. SMN protein levels were analyzed by dose response in quantitative immunoblots with statistical analysis by one-way ANOVA with post-hoc analysis using Dunnett or Bonferroni, as appropriate. Fresh media and compound were added and incubated for 48 hours. After 48 hours, cells were harvested, washed with cold phosphate-buffered saline, and lysed in Protein Lysis Buffer (150 mM NaCl, 10 mM Tris-HCl pH 8.0, 2% SDS, and protease inhibitor cocktail). Approximately 5 µg total protein per lane was found to be within the linear range for immunoblot detection of SMN and a-tubulin. Western blots were probed for SMN with the 2F1 (cell Signaling #12976) mouse monoclonal antibody and a-tubulin. Quantification of protein was performed with the Fujifilm LAS-4000 Multifunctional Imaging System. The signal intensity was measured for each band on an immunoblot, normalized to the loading control, and the fold increase was determined in relation to the appropriate DMSO-treated control. Treatment of patient-derived fibroblasts (3813 cells; SMN1−/−SMN2+/+) with compound 291-88-1 gave a dose dependent 2-3 fold increase of SMN protein expression as determined by Western blot analysis (FIG. 1B).

Figure 2:
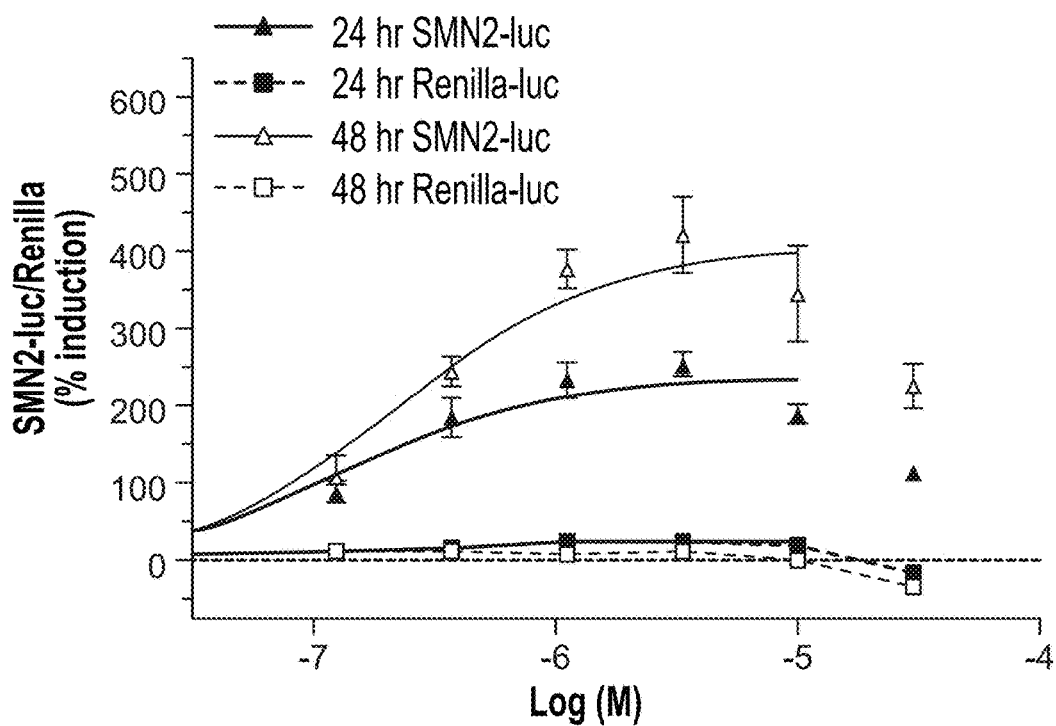
FIG. 2 is a graph depicting the concentration dependent increase in SMN-luciferase at 24 and 48 hours exposure of HEK293 SMN2 reporter cells with LDN-291-88-1.

Concentration dependent increase in SMN-luciferase at 24 and 48 hours exposure of HEK293 SMN2 reporter cells with LDN-291-88-1 was shown. There was a maximal increase of 400% greater than the DMSO control at 48 hours with 3 µM LDN 291-88-1 (FIG. 2).

Figure 3A:
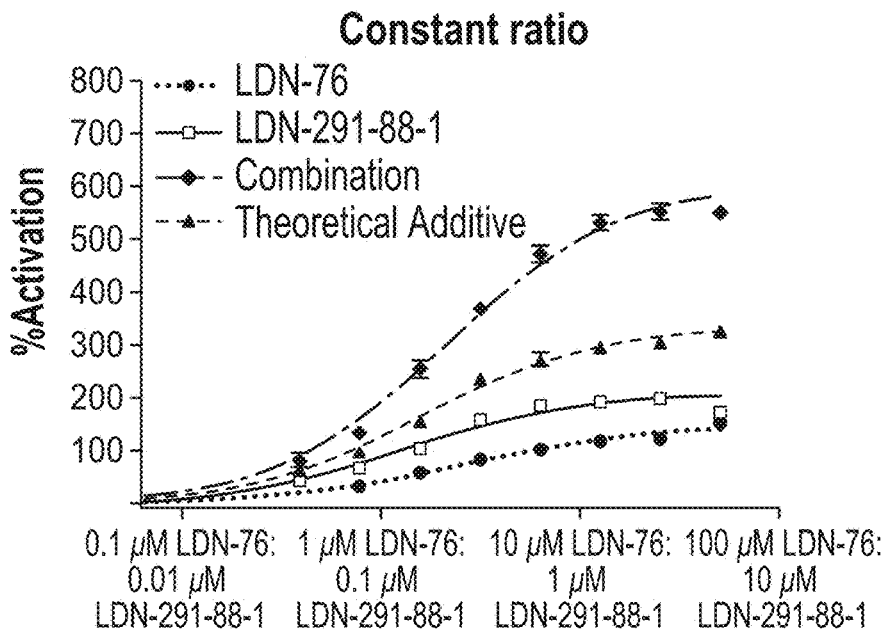
FIGS. 3A & 3B depict luciferase activity plotted versus increasing concentrations of LDN-291-88-1 and LDN-76 at two different constant ratios.
Figure 3B:
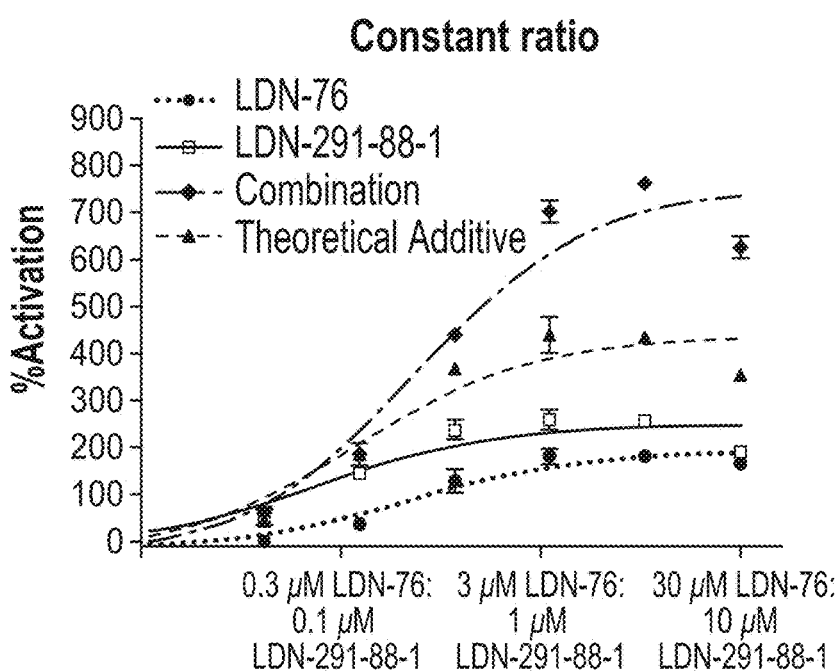

To investigate the mechanism of action of LDN291-88-1, the HEK293 SMN2 reporter cells were exposed to LDN291-88-1 at a concentration of 10 µM plus 10 µM cycloheximide to block new protein synthesis, or the same concentration of cycloheximide plus DMSO for comparison. Cell lysates were prepared at the times indicated up to 24 hours as in FIGS. 3A & 3B. The amount of SMN-luciferase protein was quantified by luciferase assay and plotted versus time. The half-life of SMN-luciferase in DMSO treated cells was 3.5 hours, while LDN291-88-1 increased its half-life to >24 hours (FIG. 3A). There was no effect on renilla luciferase (FIG. 3B). These data indicate that LDN291-88-1 acts post-transcriptionally by stabilizing the SMN protein.

Example 2

In this Example, the activity of compound 291-88-1 combined with the LDN-75 series compound LDN212104 was analyzed for additive or synergistic increases in SMN protein levels.

Evidence that the LDN-75 series compounds act post-transcriptionally and stabilize the SMN-protein, whereas LDN-76 series compounds stimulate SMN2 at the transcriptional level were previously reported (Cherry et al., EMBO Mol Med (2013) 5, pp. 1035-50). Accordingly, the compounds of the present disclosure were analyzed similarly.

The compound 291-88-1 was mixed with LDN-76 in a dose response experiment. The amplitude of SMN2-luciferase activation was enhanced (291-88-1 plus LDN-214301, purple line) in comparison to LDN-76 alone (blue) or LDN291-88-1 alone (green)). The theoretical additive is depicted in black (FIGS. 3A and 3B). It is proposed that the synergistic increase in response amplitude results from a combination of compounds that cooperate through separate mechanisms or pathways.

Figure 4:
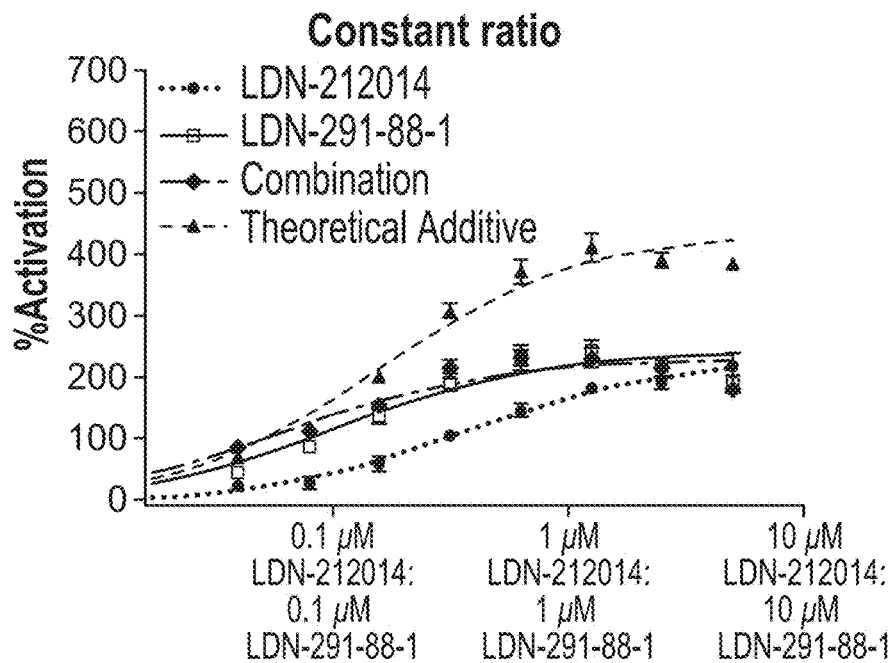
FIG. 4 depicts luciferase activity of compound 291-88-1 mixed with LDN212014.

However, when compound 291-88-1 was combined with LDN-75 (LDN212014), there was no increase in activity (FIG. 4). It is proposed that there is no response in amplitude due to the combination of two compounds with similar modes of action.

Example 3

In this Example, the activity of compound 291-88-1 combined with the LDN-76 series analog, LDN-212391, was analyzed for additive or synergistic increases in SMN protein levels.

Figure 5:
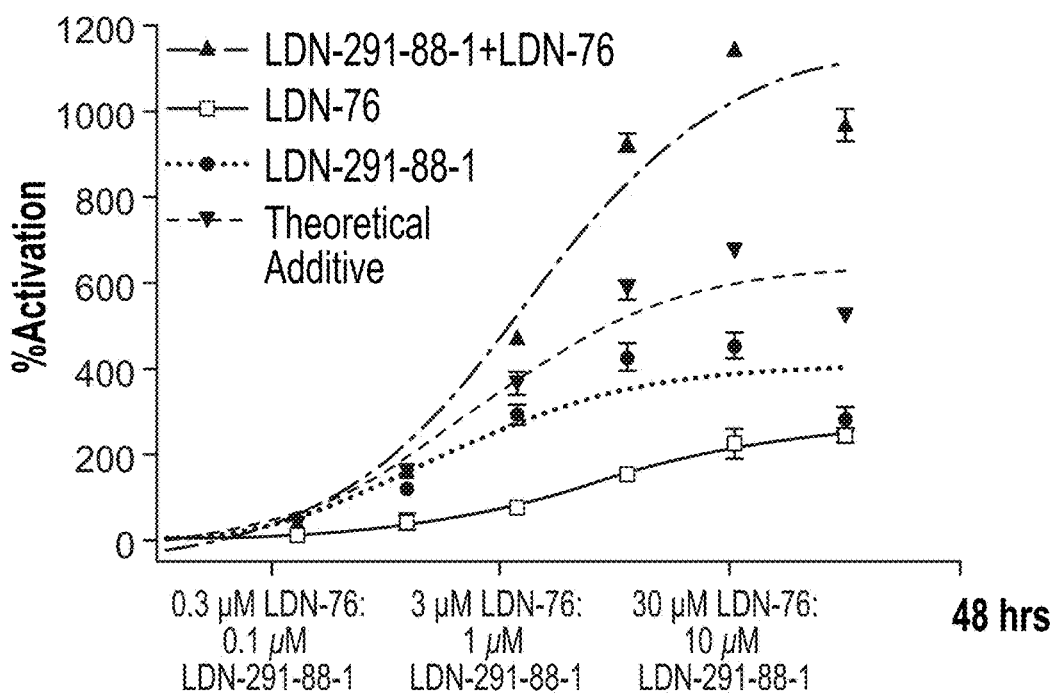
FIG. 5 depicts luciferase activity of compound 291-88-1 mixed with a LDN-76 analogue, LDN-212391, at 48 hours.

As described in Example 2, compound 291-88-1 was mixed with LDN-212391 in a dose response experiment. The amplitude of SMN2-luciferase activation was enhanced (291-88-1 plus LDN-212391, purple line) in comparison to LDN-76 alone (green) or LDN291-88-1 alone (blue)). The theoretical additive is depicted in black (FIG. 5).

Example 4

In this Example, the activity of compound 291-88-1 combined with the SMN2 splicing compound SMN-C2 was analyzed for additive or synergistic increases in SMN protein levels.

Figure 6:
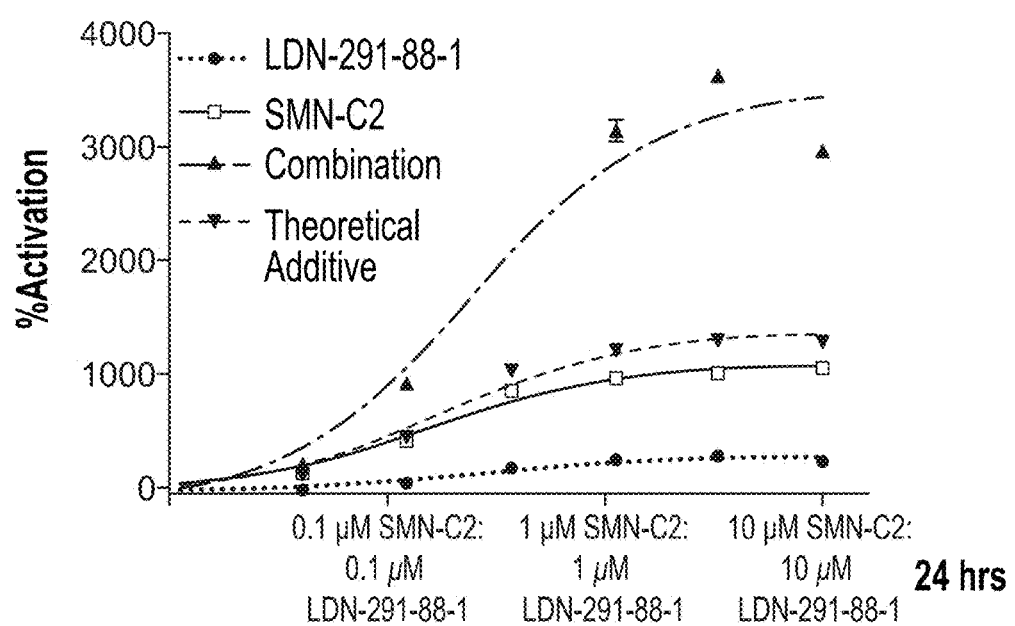
FIG. 6 depicts luciferase activity of compound 291-88-1 mixed with the SMN2 splicing compound, SMN-C2, at 24 hours.

As described in Example 2, compound 291-88-1 was mixed with SMN-C2 in a dose response experiment. The amplitude of SMN2-luciferase activation was enhanced (291-88-1 plus SMN-C2, purple line) in comparison to SMN-C2 alone (red) or LDN291-88-1 alone (blue)). The theoretical additive is depicted in black (FIG. 6). It is proposed that the synergistic increase in response amplitude results from a combination of compounds that cooperate through separate mechanisms or pathways.

Example 5

In this Example, the activity of compound 291-88-1 combined with the SMN2 splicing compound NVS-SM2 was analyzed for additive or synergistic increases in SMN protein levels.

Figure 7A:
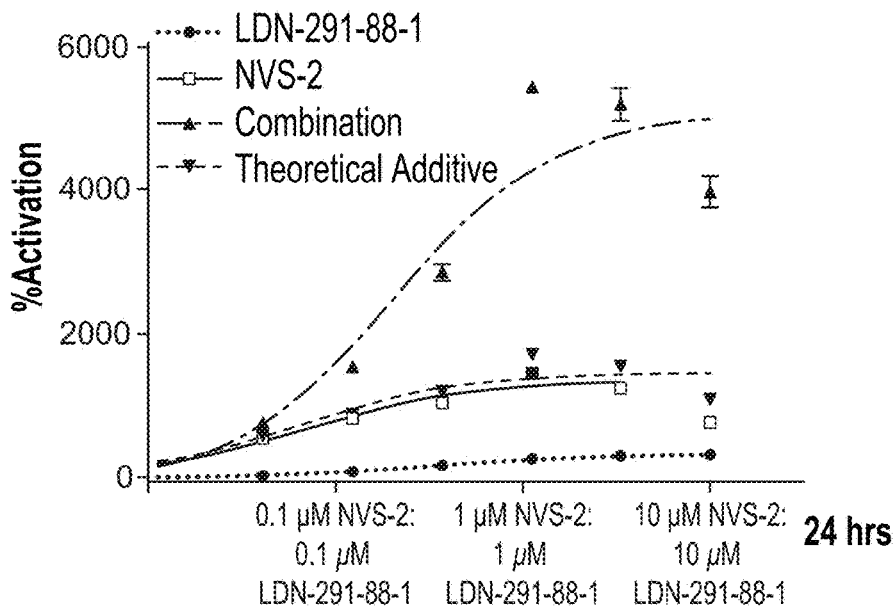
FIGS. 7A & 7B depict luciferase activity of compound 291-88-1 mixed with the SMN2 splicing compound, NVS-SM2, at 24 and 48 hours.
Figure 7B:
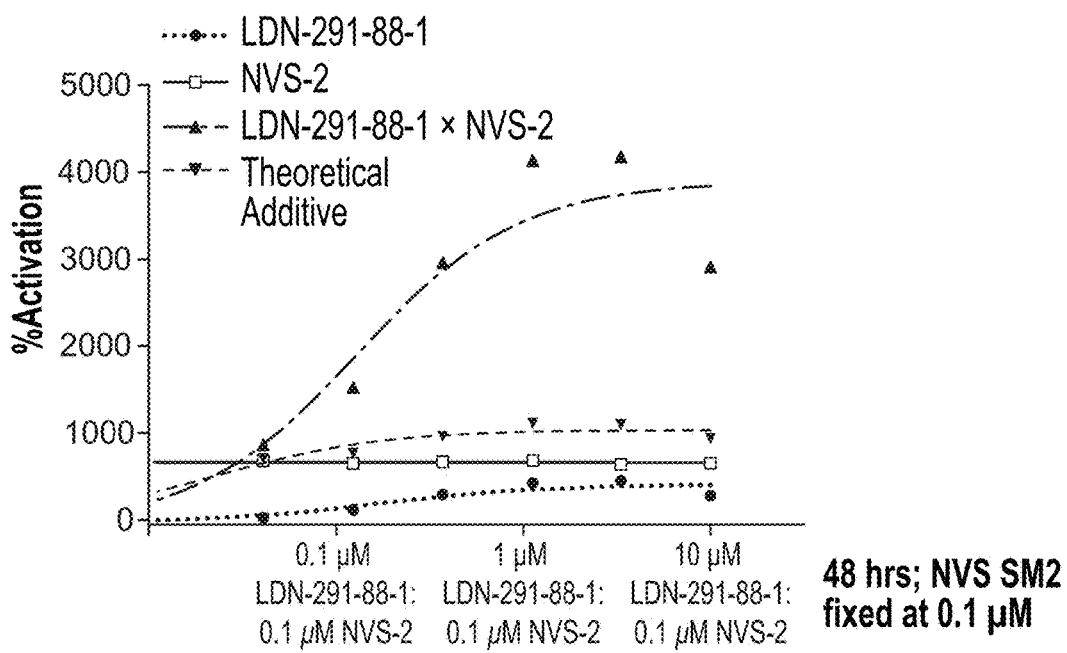

As described in Example 2, compound 291-88-1 was mixed with NVS-SM2 in a dose response experiment. The amplitude of SMN2-luciferase activation was enhanced (291-88-1 plus NVS-SM2, purple line) in comparison to NVS-SM2 alone (red) or LDN291-88-1 alone (blue)). The theoretical additive is depicted in black (FIGS. 7A and 7B). It is proposed that the synergistic increase in response amplitude results from a combination of compounds that cooperate through separate mechanisms or pathways.

Example 6

In this Example, the activity of LDN-76 series analog, LDN-212391, combined with the SMN2 splicing compound SMN-C2 was analyzed for additive or synergistic increases in SMN protein levels.

Figure 8:
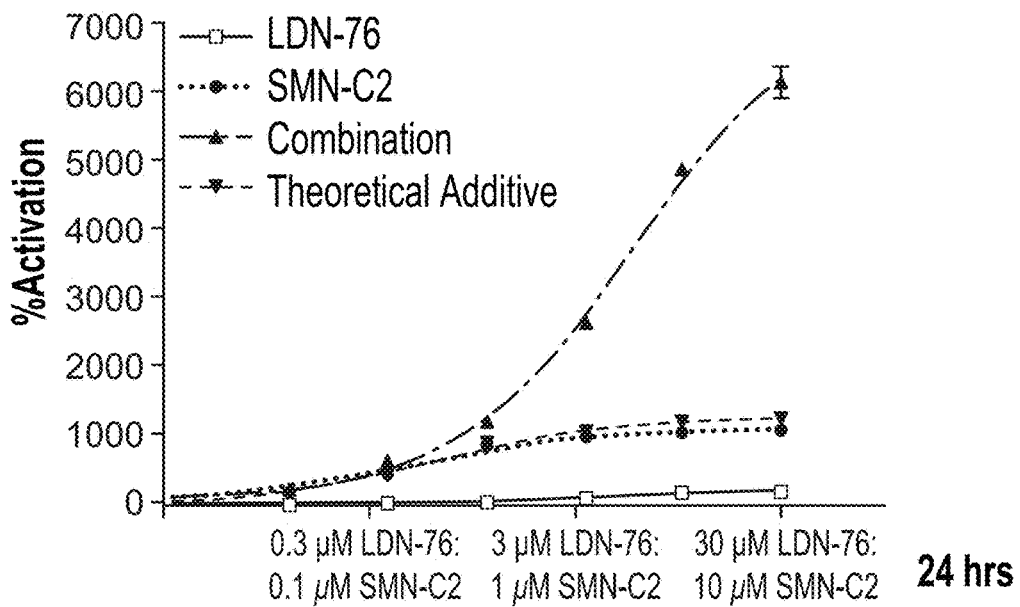
FIG. 8 depicts luciferase activity of LDN-76 analogue, LDN-212391, mixed with the SMN2 splicing compound, SMN-C2.

As described in Example 2, LDN-212391 was mixed with SMN-C2 in a dose response experiment. The amplitude of SMN2-luciferase activation was enhanced (LDN-212391 plus SMN-C2, purple line) in comparison to SMN-C2 alone (red) or LDN-21391 alone (green)). The theoretical additive is depicted in black (FIG. 8). It is proposed that the synergistic increase in response amplitude results from a combination of compounds that cooperate through separate mechanisms or pathways.

Example 7

In this Example, the activity of LDN-76 series analog, LDN-212391, combined with the SMN2 splicing compound, NVS-SM2, was analyzed for additive or synergistic increases in SMN protein levels.

Figure 9A:
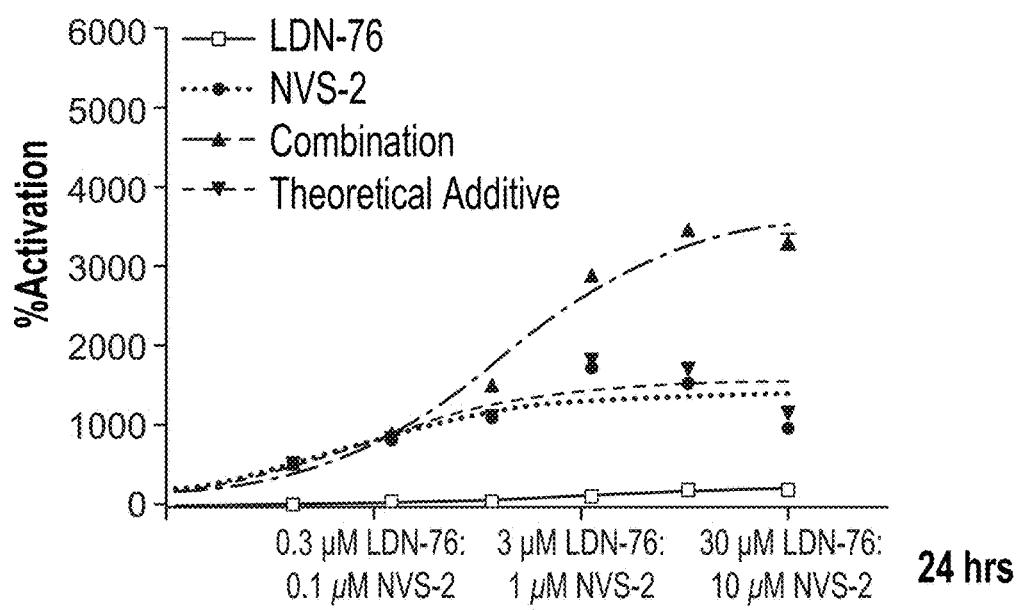
FIGS. 9A & 9B depict luciferase activity of LDN-76 analogue, LDN-212391, mixed with the SMN2 splicing compound, NVS-SM2.
Figure 9B:
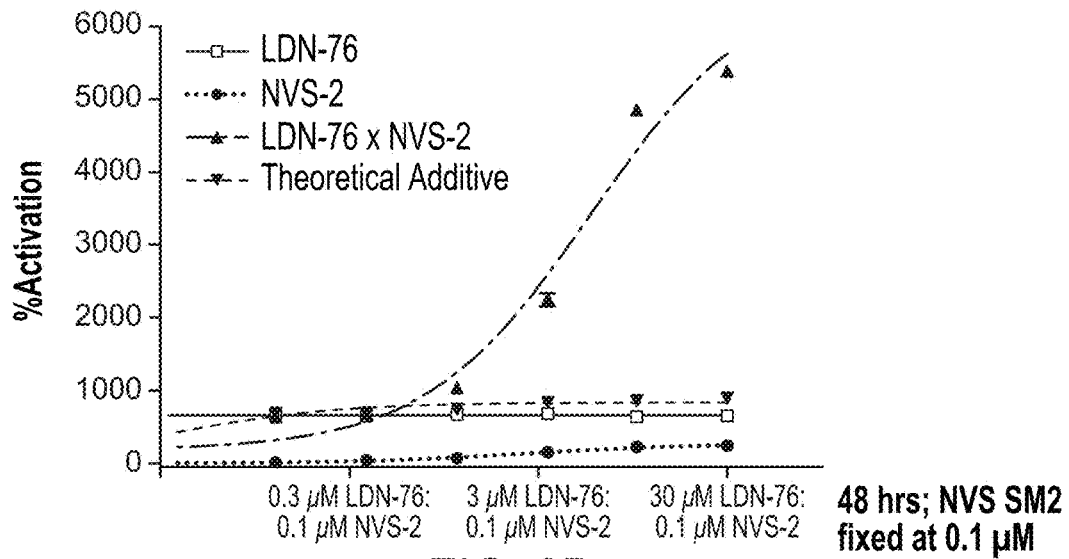

As described in Example 2, LDN-212391 was mixed with NVS-SM2 in a dose response experiment. The amplitude of SMN2-luciferase activation was enhanced (LDN-212391 plus NVS-SM2, purple line) in comparison to NVS-SM2 alone (red) or LDN291-88-1 alone (blue)). The theoretical additive is depicted in black (FIGS. 9A and 9B). It is proposed that the synergistic increase in response amplitude results from a combination of compounds that cooperate through separate mechanisms or pathways.

Example 8

In this Example, the activity of compound 291-88-1 combined with both the LDN-76 series analog LDN-212391 and the SMN2 splicing compound NVS-SM2 was analyzed for additive or synergistic increases in SMN protein levels.

Figure 10:
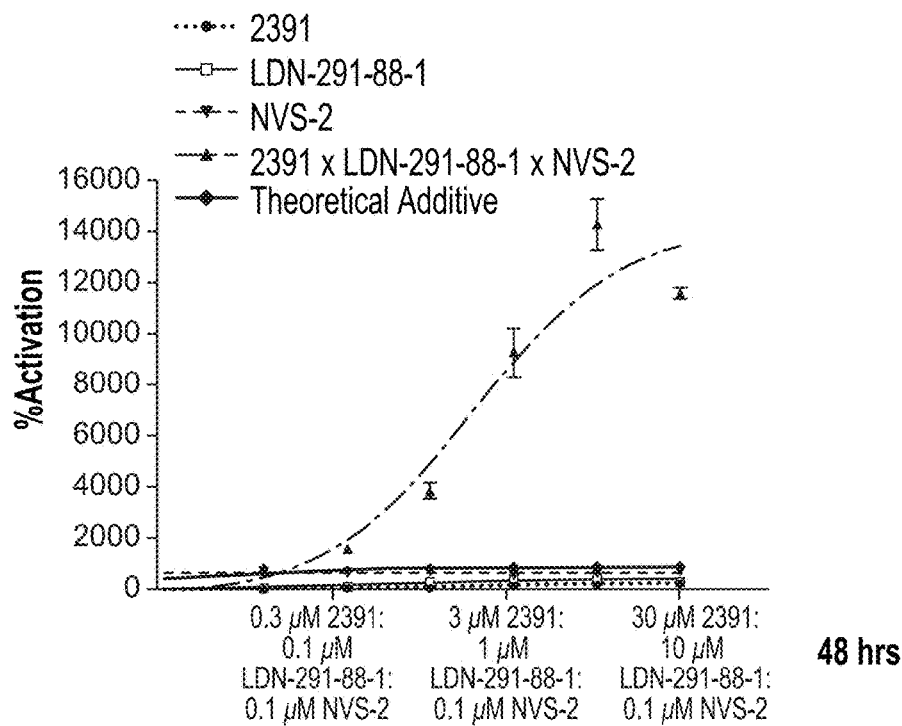
FIG. 10 depicts luciferase activity of compound 291-88-1 mixed with the LDN-76 analogue, LDN-212391, and the SMN2 splicing compound, NVS-SM2.

As described in Example 2, compound 291-88-1 was mixed with LDN-212391 and NVS-SM2 in a dose response experiment. The amplitude of SMN2-luciferase activation was enhanced (291-88-1 plus LDN-212391 plus NVS-SM2, purple line) in comparison to LDN-76 alone (green), NVS-SM2 (red) or LDN291-88-1 alone (blue)). The theoretical additive is depicted in black (FIG. 10).

Example 9

In this Example, the in vivo survival effect of compound 291-88-1 was analyzed in mice.

Figure 11:
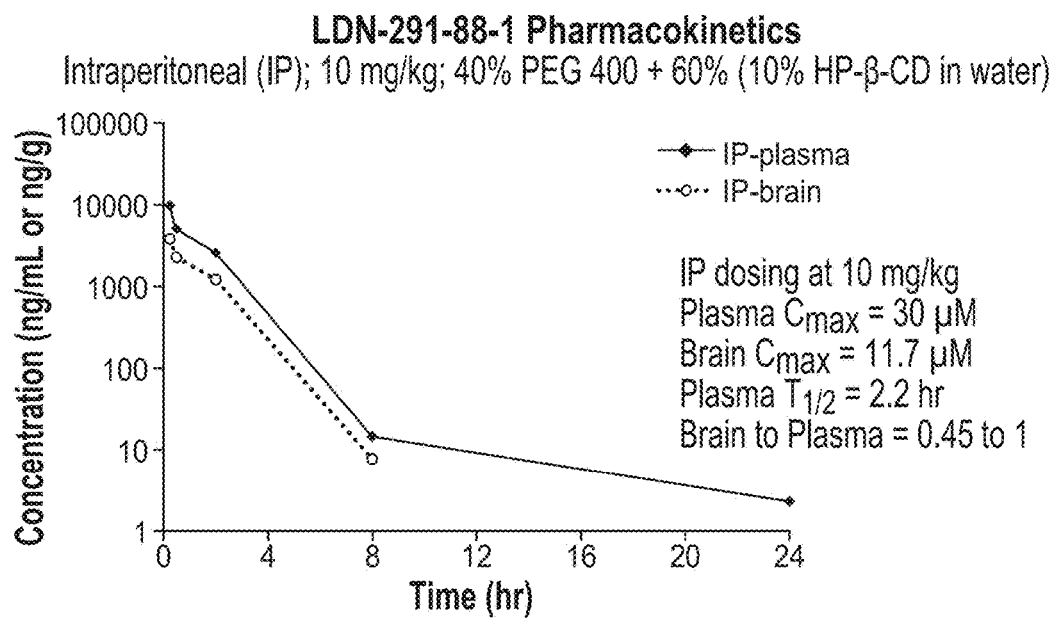
FIG. 11 depicts LDN-291-88-1 pharmacokinetics when intraperitoneally (IP) administered into normal adult C57BL/6 mice.
Figure 12:
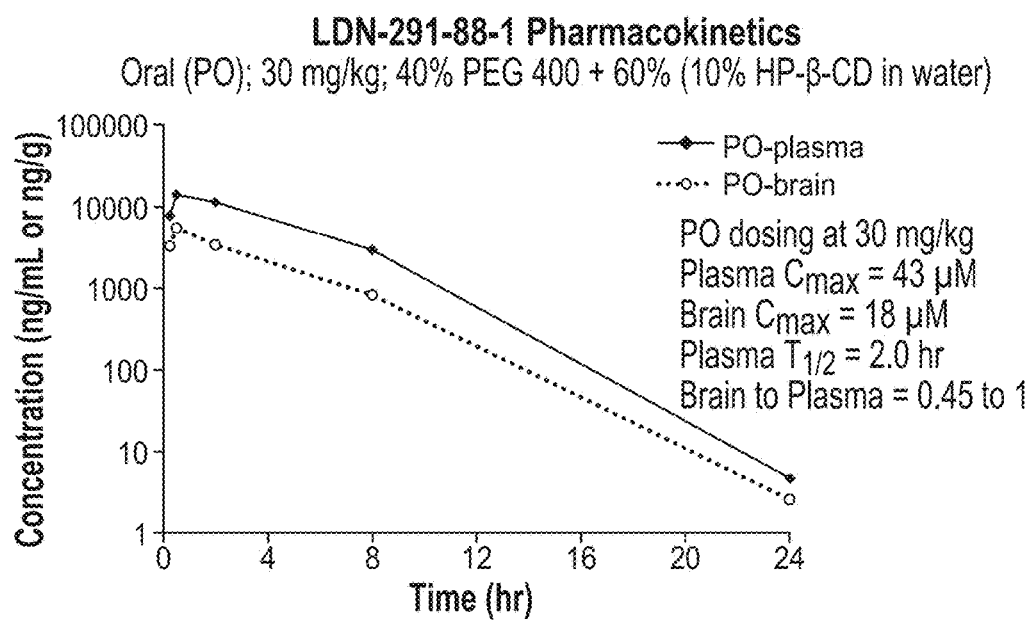
FIG. 12 depicts LDN-291-88-1 pharmacokinetics when orally (PO) administered into normal adult C57BL/6 mice.

Compound 291-88-1 was administered either by intraperitoneal (IP) or oral (PO) administration into normal adult C57BL/6 mice. Pharmacokinetic data for both administration means is shown in FIGS. 11 & 12.

Figure 13:
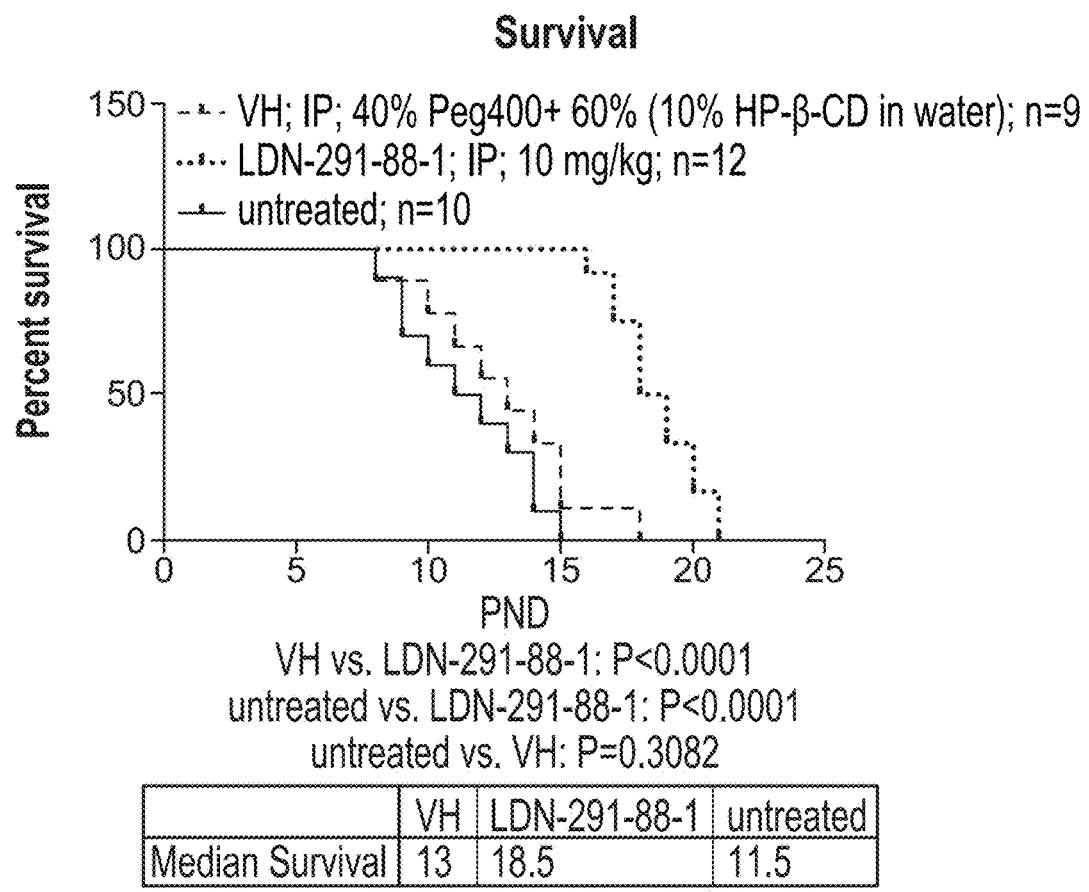
FIG. 13 depicts survival of animals administered LDN-291-88-1 as compared to that of untreated animals and vehicle (VH) treated animals.

Compound 291-88-1 was administered either by intraperitoneal (IP) administration into the SMA mice SMNΔ7 FVB.SMNΔ7; SMN2; Smn (Jackson Laboratories 005025). Daily treatment of SMNΔ7 animals with 10 mg/kg (IP) was continued as long as feasible. The lifespan of treated animals was compared to that of untreated animals and vehicle (VH) treated animals (FIG. 13). VH treated animals included treatment with 40% PEG400+60% (10% HP-β-CD in water). The median survival of untreated animals was 11.5 days, while VH-treated animals had a median survival of 13 days (not statistically significant, p=0.31). Treatment with compound 291-88-1 increased median survival to 18.5 days, p<0.0001.

Example 10

In this Example, the in vivo effect of compound 291-88-1 in mice was evaluated.

Figure 14:
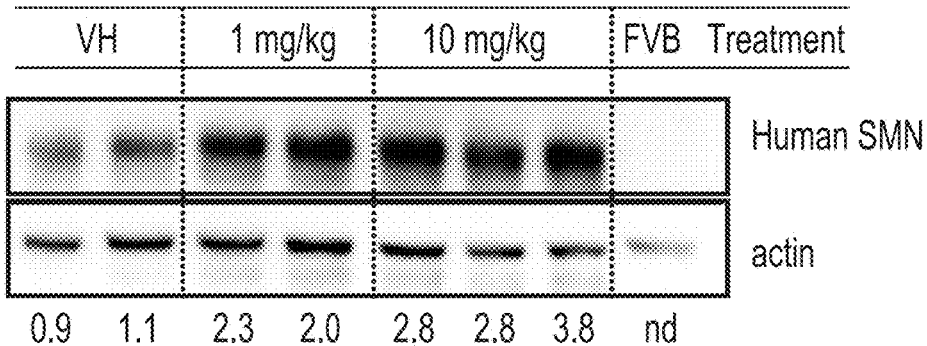
FIG. 14 is a Western blot depicting brain extracts for total SMN protein in comparison to the housekeeping gene, actin.
Figure 15:
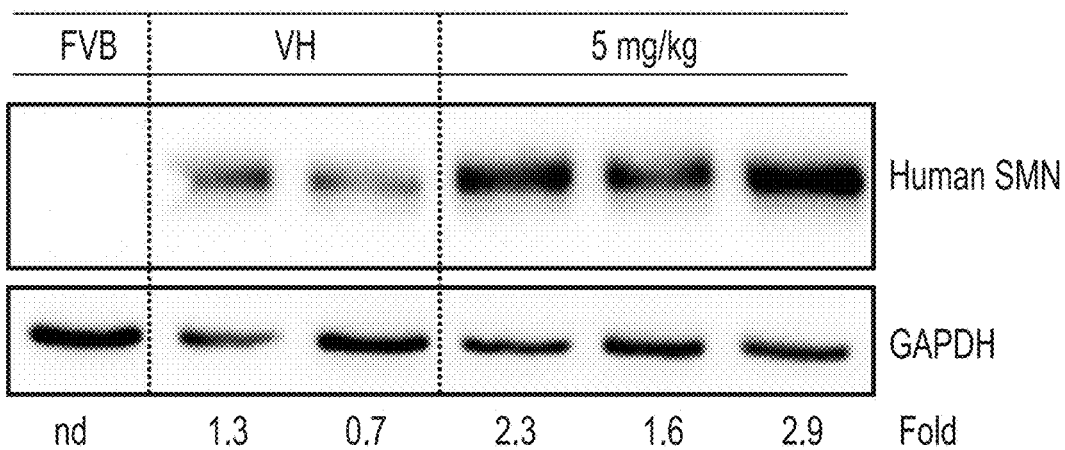
FIG. 15 is a Western blot depicting brain extracts for total SMN protein in comparison to the housekeeping gene, GAPDH.

Animals were treated once daily (subcutaneous injection or oral) for 5 days, starting on postnatal day 2 (PND) with increasing doses of 291-88-1. On PND7, mice were sacrificed and tissues were harvested. Tissues were harvested from treated animals on PND 7 and compared to tissues from non-transgenic control mice (FVB) and VH (vehicle: PEG:PBS 50:50) treated animals. Brain extracts were assayed for total SMN protein in comparison to the housekeeping genes, actin and GAPDH (FIGS. 14 and 15, respectively). There was a dose-dependent increase in SMN protein levels ranging from 2-3 fold.

Example 11

In this Example, various analogs of compound 298-898-1 will be produced.

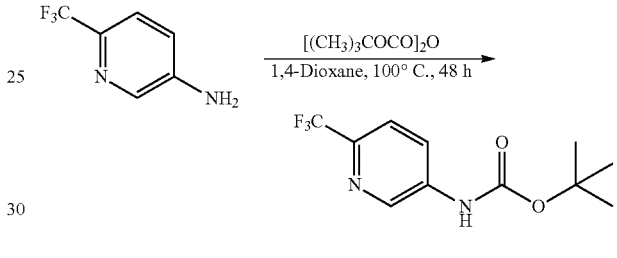

Tert-butyl
(6-(trifluoromethyl)pyridin-3-yl)carbamate 6-(trifluoromethyl)pyridin-3-amine (5 g, 30.8 mmol) and di-tert-butyl dicarbonate (6.73 g, 30.8 mmol) were dissolved in 1,4-dioxane (30 mL). The reaction was refluxed at 100° C. for 48 hours. Another half-equivalent of di-tert-butyl dicarbonate was added to the solution after 8 hours and 24 hours of stirring. The mixture was cooled to room temperature. An excess of ethyl acetate was added and the reaction was washed with brine twice. The organic layer was dried over MgSO$_4$, concentrated down, and recrystallized in a 10:1 cyclohexane/ethyl acetate mixture to yield product. Yield: 70%. $^1$H NMR (400 MHz, DMSO): 10.00 (s, 1H), 8.73 (d, J=2.43 Hz, 1H), 8.11 (dd, J=8.65, 2.24 Hz, 1H), 7.79 (d, J=8.65 Hz, 1H), 1.48 (s, 9H). [M+1]$^+$=262.1.

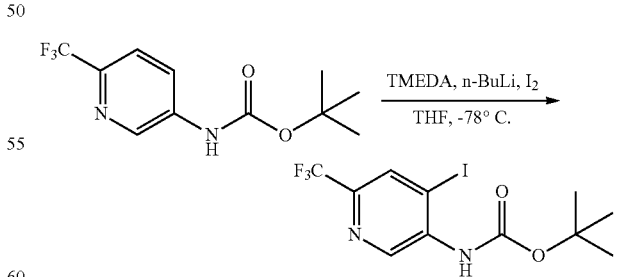

Tert-butyl
(4-iodo-6-(trifluoromethyl)pyridin-3-yl)carbamate

Under an inert atmosphere, tert-butyl (6-(trifluoromethyl)pyridin-3-yl)carbamate (2.5 g, 9.53 mmol) was dissolved in anhydrous tetrahydrofuran (50 mL). TMEDA (2.55 g, 21.93 mmol) was added to the solution, which was then cooled to −78° C. using an acetone/dry ice bath and stirred for 30 minutes. n-BuLi (10.95 mL, 21.93 mmol) was added drop-wise over 15 minutes, and the solution was stirred for an additional 30 minutes at −78° C. The round-bottom flask was then transferred to a salted ice bath to stir for 30 minutes at −10° C. The reaction solution was cooled to −78° C. before adding drop-wise a solution of iodine (3.63 g, 14.3 mmol) dissolved in tetrahydrofuran (10 mL). The reaction was stirred overnight until reaching room temperature. The mixture was quenched with saturated $KHSO_3$ (10 mL) and the product was washed with saturated NaCl and recovered with ethyl acetate. The organic layer was dried over $MgSO_4$ and concentrated down. The crude product was purified by chromatography on silica gel (cyclohexane/ethyl acetate: 95/5) and dried under vacuum. Yield: 35%. $^1$H NMR (400 MHz, DMSO): 9.07 (s, 1H), 8.62 (s, 1H), 8.36 (s, 1H), 1.48 (s, 9H). [M+1]$^+$=389.0.

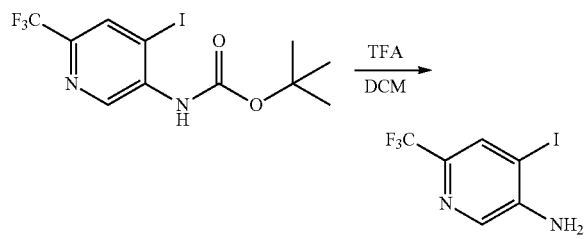

4-iodo-6-(trifluoromethyl)pyridin-3-amine

Tert-butyl (4-iodo-6-(trifluoromethyl)pyridin-3-yl)carbamate (2.5 g, 6.44 mmol) was dissolved in dichloromethane (45 mL). Trifluoroacetic acid (3.67 g, 32.2 mmol) was added to the solution. The solution was stirred at 21° C. for 24 hours. The solution was then taken up in excess dichloromethane and washed with saturated NaCl. The organic layer was dried over $MgSO_4$ and concentrated down. The crude product was purified by chromatography on silica gel (cyclohexane/ethyl acetate 80/20) and dried under vacuum. Yield: 91%. $^1$H NMR (400 MHz, DMSO): 8.0 (s, 1H), 7.95 (s, 1H), 6.21 (s, 2H). [M+1]$^+$=289.0.

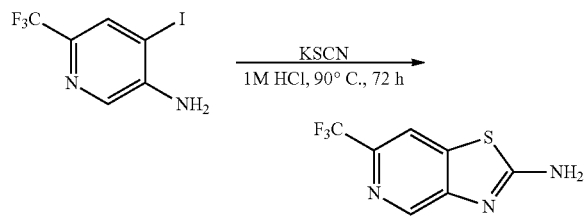

6-(trifluoromethyl)thiazolo[4,5-c]pyridin-2-amine

Potassium thiocyanate (1.01 g, 10.4 mmol) was dissolved in a 1 M solution of hydrochloric acid (24 mL). 4-iodo-6-(trifluoromethyl)pyridin-3-amine (1.5 g, 5.2 mmol) was added, and the solution was heated at 90° C. for 48 hours. After being cooled to room temperature, the solution was neutralized with saturated $NaHCO_3$ until the pH equaled 7. The solution was taken up in ethyl acetate and the two layers were separated. The aqueous layer was treated with an excess of ethyl acetate to extract more product. All of the organic layers were combined, washed with saturated NaCl, dried over $MgSO_4$, and concentrated down. The crude product was purified by chromatography on silica gel (cyclohexane/ethyl acetate 50/50) and dried under vacuum. Yield: 58%. $^1$H NMR (400 MHz, DMSO): 8.64 (s, 1H), 8.33 (s, 1H), 8.15 (s, 2H). [M+1]$^+$=221.1.

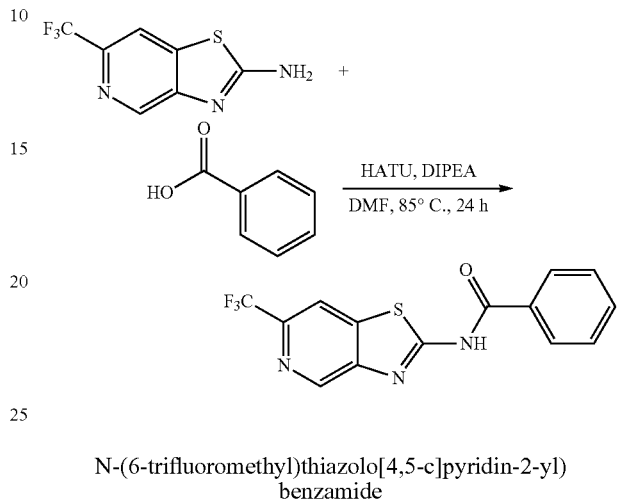

N-(6-trifluoromethyl)thiazolo[4,5-c]pyridin-2-yl) benzamide

N,N-Diisopropylethylamine (DIPEA) (258 mg, 2.0 mmol) was slowly added drop-wise to a solution of 1-[bis(dimethylamino)methylene]-1H-1,2,3-triazolo[4,5-b]pyridinium 3-oxid hexafluorophosphate (HATU) (570 mg, 1.5 mmol) in of DMF (2 mL). The solution was stirred for 5 minutes and then added drop-wise to a mixture of the appropriate carboxylic acid (122 mg, 1.0 mmol) and 6-(trifluoromethyl)thiazolo[4,5-c]pyridine-2-amine (220 mg, 1.0 mmol) in a reaction vial. The solution was stirred at 85° C. for 24 hours. After cooling the reaction to room temperature, the reaction was taken up in ethyl acetate and washed with saturated $NH_4Cl$, saturated $NaHCO_3$, and saturated NaCl. All of the organic layers were combined, dried over $MgSO_4$, and concentrated down. The crude product was purified by chromatography on silica gel (cyclohexane/ethyl acetate 65/35) and dried under vacuum. Yield: 43%. $^1$H NMR (400 MHz, DMSO): 13.333 (s, 1H), 9.165 (s, 1H), 8.720 (d, J=0.56, 1H), 8.150 (dt, J=8.25, 1.59 Hz, 2H), 7.686 (m, 1H), 7.582 (m, 2H). [M+1]$^+$=324.1.

OR

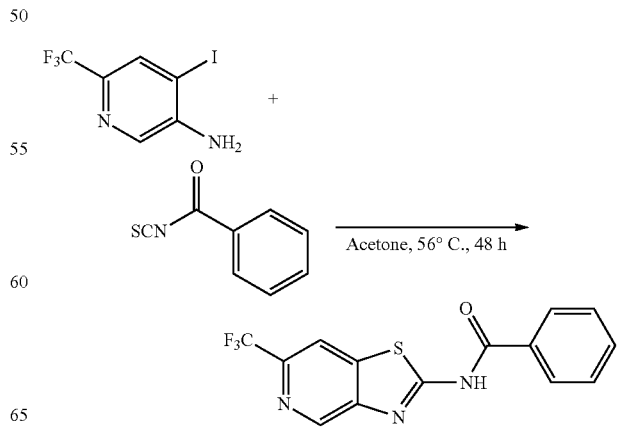

N-(6-trifluoromethyl)thiazolo[4,5-c]pyridin-2-yl)benzamide 4-iodo-6-(trifluoromethyl)pyridin-3-amine (144 mg, 0.5 mmol) was dissolved in acetone (15 mL). Benzoyl isothiocyanate (163 mg, 1.0 mmol) was added and the solution was refluxed for 48 hours. After cooling the solution to room temperature, the product precipitated out of solution. The solid was dried under vacuum. Yield: 90%. $^1$H NMR (400 MHz, DMSO): 13.333 (s, 1H), 9.165 (s, 1H), 8.720 (d, J=0.56, 1H), 8.150 (dt, J=8.25, 1.59 Hz, 2H), 7.686 (m, 1H), 7.582 (m, 2H). [M+1]$^+$=324.1.

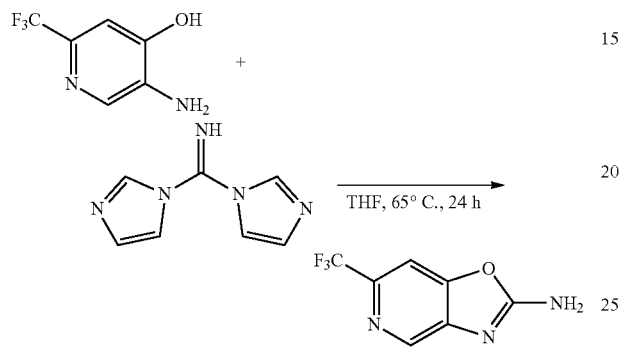

6-(trifluoromethyl)oxazolo[4,5-c]pyridin-2-amine 5-amino-2-(trifluoromethyl)pyridine-4-ol (220 mg, 1.24 mmol) was dissolved in anhydrous THF (7 mL). Di(1H-imidazol-1-yl)methanimine was then dissolved into the solution. The reaction was stirred at 65° C. for 24 hours. After cooling the solution to room temperature, the solution was taken up in ethyl acetate and washed with deionized water, saturated NH$_4$Cl, and saturated NaCl. The organic layer was dried over MgSO$_4$, filtered, and concentrated down to the crude material. Excess CH$_2$Cl$_2$ was added to the crude solid, which precipitated out. The pure solid was filtered and dried under vacuum. Yield: 91%. $^1$H NMR (400 MHz, DMSO): 8.58 (s, 1H), 8.17 (s, 2H), 8.02 (s, 1H). [M+1]$^+$=204.1.

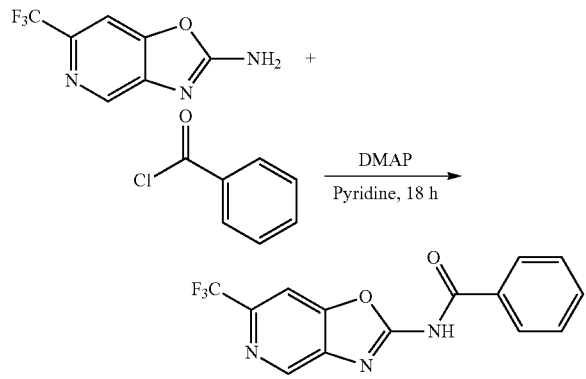

N-(6-(trifluoromethyl)oxazolo[4,5-c]pyridin-2-yl)benzamide 6-(trifluoromethyl)oxazolo[4,5-c]pyridine-2-amine (70 mg, 0.34 mmol) and 4-(dimethylamino)pyridine (4.21 mg, 10% mmol) were dissolved in anhydrous pyridine (2 mL) and cooled to 0° C. under nitrogen. Benzoyl chloride (48.4 mg, 0.34 mmol) was added drop-wise to the stirring solution. The reaction was warmed to room temperature and stirred for an additional 18 hours. The solution was then concentrated down and taken up in DCM. The organic layer was washed with deionized water, saturated NaHCO$_3$, and saturated NaCl. The organic layer was dried over MgSO$_4$ and concentrated down to the crude material. The crude product was purified by chromatography on silica gel (cyclohexane/ethyl acetate: 80/20) and dried under vacuum. Yield: 20%. $^1$H NMR (400 MHz, DMSO): 8.97 (s, 1H), 8.34 (s, 1H), 8.05 (d, J=7.35 Hz, 2H), 7.56-7.53 (m, 3H). [M+1]$^+$=308.1.

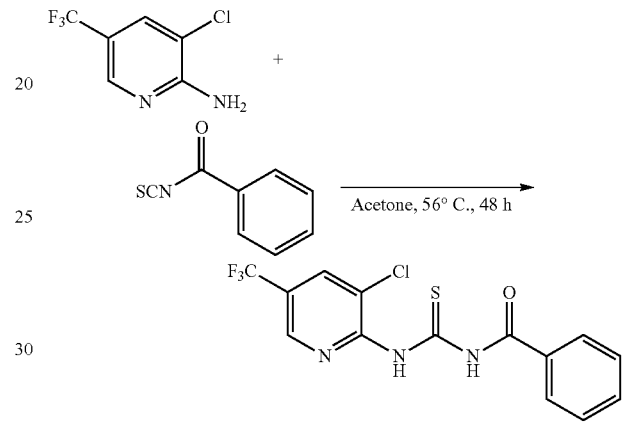

N-((3-chloro-5-(trifluoromethyl)pyridin-2-yl)carbamothioyl)benzamide 3-chloro-5-(trifluoromethyl)pyridin-2-amine (5.88 g, 30 mmol) and benzoyl isothiocyanate (7.34 g, 45 mmol) were dissolved in acetone (50 mL). The solution was refluxed for 48 hours. After the reaction was cooled to room temperature, the solution was concentrated down to yellow oil. The crude material was taken up in ethyl acetate (200 mL) and saturated NaCl. The organic layer was collected, dried over MgSO$_4$, and concentrated down. A TLC was taken in 4:1 hexanes/ethyl acetate to confirm purity. Yellow solid was collected by filtration. Yield: 93%. $^1$H NMR (400 MHz, DMSO): 12.58 (s, 1H), 12.00 (s, 1H), 8.92 (d, J=0.85 Hz, 1H), 8.65 (d, J=1.46 Hz, 1H), 8.01 (d, J=7.38 Hz, 2H), 7.68 (t, J=7.43 Hz, 1H), 7.56 (t, J=7.76 Hz, 2H). [M+1]$^+$=360.1.

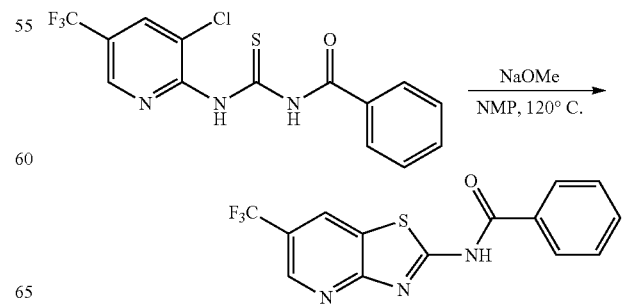

N-(6-(trifluoromethyl)thiazolo[4,5-b]pyridin-2-yl)benzamide

N-((3-chloro-5-(trifluoromethyl)pyridin-2-yl)carbamothioyl)benzamide (10 g, 31 mmol) and sodium methoxide (3.24 g, 60 mmol) were dissolved in methylpyrrolidone (60 mL). The solution was stirred at 120° C. for 2 hours. After the solution was cooled to room temperature, the reaction was poured into water. The solid was filtered and dried. Yield: 30%. $^1$H NMR (500 MHz, DMSO): 13.46 (s, 1H), 9.01 (s, 1H), 8.94 (s, 1H), 8.18 (d, J=7.31 Hz, 2H), 7.71 (t, J=7.38 Hz, 1H), 7.60 (t, J=7.71 Hz, 2H). [M+1]$^+$=324.1.

General procedure for synthesizing the amide analogs

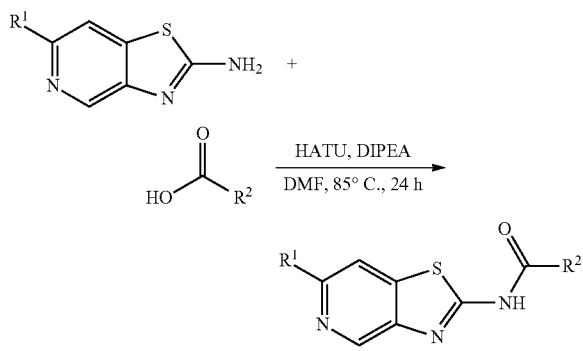

N,N-Diisopropylethylamine (DIPEA) (258 mg, 2.0 mmol) was slowly added drop-wise to a solution of 1-[Bis(dimethylamino)methylene]-1H-1,2,3-triazolo[4,5-b]pyridinium 3-oxid hexafluorophosphate (HATU) (570 mg, 1.5 mmol) in DMF (2 mL). The solution was stirred for 5 minutes and then added drop-wise to a mixture of the appropriate carboxylic acid (1.0 mmol) and the thiazolo[4,5-c]pyridine-2-amine derivative (1.0 mmol) in a reaction vial. The solution was stirred at 85° C. for 24 hours. The reaction was monitored by TLC or LCMS. The product was first worked up in ethyl acetate and washed with saturated ammonium chloride, saturated sodium bicarbonate, and saturated sodium chloride then isolated and purified by silica gel chromatography using appropriate cyclohexane and ethyl acetate mixtures.

The following compounds were prepared using the general procedures described above.

N-(6-(trifluoromethyl)thiazolo[4,5-c]pyridine-2-yl)benzamide

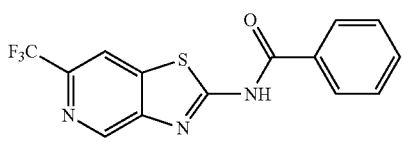 [SMILES: O=C(Nc1nc2cnc(C(F)(F)F)cc2s1)c1ccccn1]

$^1$H NMR (400 MHz, DMSO): 13.35 (s, 1H), 9.18 (s, 1H), 8.74 (s, 1H), 8.17 (td, J=7.74, 1.66 Hz, 2H), 7.7 (t, J=7.4 Hz, 1H), 7.6 (t, J=7.57 Hz, 2H). [M+1]$^+$=324.1

N-(6-(trifluoromethyl)thiazolo[4,5-c]pyridin-2-yl)picolinamide

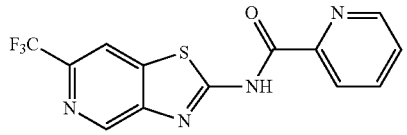

$^1$H NMR (500 MHz, DMSO): 9.20 (s, 1H), 8.82 (d, J=3.85 Hz, 1H), 8.76 (s, 1H), 8.25 (d, J=7.73 Hz, 1H), 8.14 (t, J=7.32 Hz, 1H), 7.78 (t, J=5.81 Hz, 1H). [M+1]$^+$=325.1

N-(6-(trifluoromethyl)thiazolo[4,5-c]pyridin-2-yl)nicotinamide

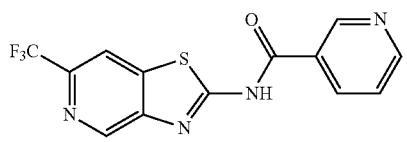

$^1$H NMR (400 MHz, DMSO): 13.55 (s, 1H), 9.27 (d, J=1.69 Hz, 1H), 9.21 (s, 1H), 8.85 (dd, J=4.82, 1.61 Hz, 1H), 8.76 (s, 1H), 8.49 (dt, J=8.14, 1.98 Hz, 1H), 7.64 (ddd, J=7.99, 4.84, 0.65 Hz, 1H). [M+1]$^+$=325.1

N-(6-(trifluoromethyl)thiazolo[4,5-c]pyridin-2-yl)pyrimidine-2-carboxamide

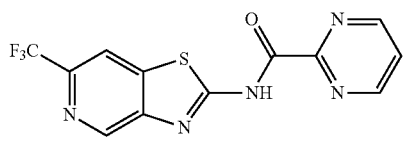 [SMILES: O=C(Nc1nc2cnc(C(F)(F)F)cc2s1)c1ncccn1]

$^1$H NMR (500 MHz, DMSO): 13.285 (s, 1H), 9.22 (s, 1H), 9.11 (d, J=4.88 Hz, 2H), 8.77 (d, J=0.46 Hz, 1H), 7.91 (t, J=4.88 Hz, 1H). [M+1]$^+$=326.1

N-(6-(trifluoromethyl)thiazolo[4,5-c]pyridin-2-yl)pyrimidine-5-carboxamide

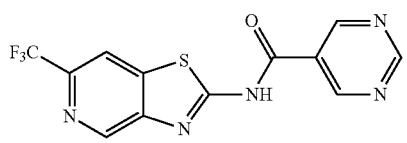

$^1$H NMR (400 MHz, DMSO): 13.72 (s, 1H), 9.43 (s, 1H), 9.41 (s, 2H), 9.21 (s, 1H), 8.76 (s, 1H). [M+1]$^+$=326.1

3-chloro-4-fluoro-N-(6-(trifluoromethyl)thiazolo[4,5-c]pyridin-2-yl)benzamide

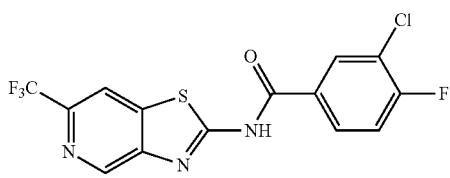 [SMILES: O=C(Nc1nc2cnc(C(F)(F)F)cc2s1)c1ccc(F)c(Cl)c1]

¹H NMR (400 MHz, DMSO): 13.44 (s, 1H), 9.18 (s, 1H), 8.73 (s, 1H), 8.42 (dd, J=7.1, 2.3 Hz, 1H), 8.19-8.16 (m, 1H), 7.65 (t, J=8.9 Hz, 1H). [M+1]⁺=376.0

4-chloro-N-(6-(trifluoromethyl)thiazolo[4,5-c]pyridin-2-yl)benzamide

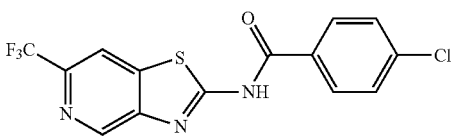 [SMILES: O=C(Nc1nc2cnc(C(F)(F)F)cc2s1)c1ccc(Cl)cc1]

¹H NMR (400 MHz, Acetone): 11.97 (s, 1H), 9.10 (s, 1H), 8.59 (s, 1H), 8.27 (d, J=8.7 Hz, 2H), 7.68 (d, J=8.7 Hz, 2H). [M+1]⁺=358.1

N-(6-(trifluoromethyl)thiazolo[4,5-c]pyridin-2-yl)thiazole-4-carboxamide

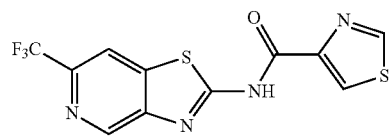 [SMILES: O=C(Nc1nc2cnc(C(F)(F)F)cc2s1)c1cscn1]

¹H NMR (400 MHz, CDCl₃): 10.75 (s, 1H), 9.18 (s, 1H), 8.92 (d, J=2.0 Hz, 1H), 8.48 (d, J=2.0 Hz, 1H), 8.22 (s, 1H). [M+1]⁺=331.0

4-fluoro-N-(6-(trifluoromethyl)thiazolo[4,5-c]pyridin-2-yl)benzamide

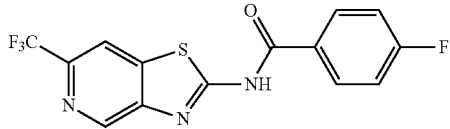 [SMILES: O=C(Nc1nc2cnc(C(F)(F)F)cc2s1)c1ccc(F)cc1]

¹H NMR (400 MHz, acetone): 11.90 (s, 1H), 9.09 (s, 1H), 8.58 (s, 1H), 8.34 (dd, J=8.8, 5.3 Hz, 2H), 7.4 (t, J=8.8 Hz, 2H). [M+1]⁺=342.0, 343.1, 344.0

N-(6-(trifluoromethyl)thiazolo[4,5-c]pyridin-2-yl)thiazole-2-carboxamide

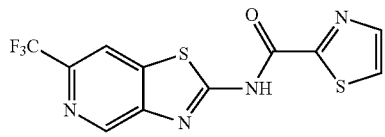 [SMILES: O=C(Nc1nc2cnc(C(F)(F)F)cc2s1)c1nccs1]

¹H NMR (400 MHz, CDCl₃): 10.70 (s, 1H), 9.20 (s, 1H), 8.23 (s, 1H), 8.06 (d, J=3.0 Hz, 1H), 7.82 (d, J=3.0 Hz, 1H). [M+1]⁺=331.0

N-(6-(trifluoromethyl)thiazolo[4,5-c]pyridin-2-yl)oxazole-5-carboxamide

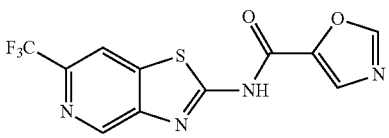 [SMILES: O=C(Nc1nc2cnc(C(F)(F)F)cc2s1)c1cnco1]

¹H NMR (400 MHz, DMSO): 13.65 (s, 1H), 9.20 (s, 1H), 8.81 (s, 1H), 8.75 (s, 1H), 8.37 (s, 1H). [M+1]⁺=315.1

N-(6-(trifluoromethyl)thiazolo[4,5-c]pyridin-2-yl)oxazole-4-carboxamide

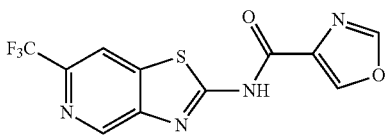

¹H NMR (400 MHz, DMSO): 13.20 (s, 1H), 9.20 (s, 1H), 9.13 (s, 1H), 8.75 (s, 1H), 8.70 (s, 1H). [M+1]⁺=315.1

N-(6-(trifluoromethyl)thiazolo[4,5-c]pyridin-2-yl)isoxazole-3-carboxamide

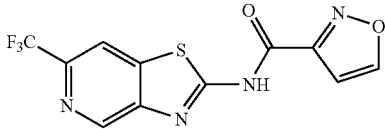

¹H NMR (400 MHz, DMSO): 13.75 (s, 1H), 9.25 (d, J=1.76 Hz, 1H), 9.22 (s, 1H), 8.76 (s, 1H), 7.26 (d, J=1.7 Hz, 1H). [M+1]⁺=315.1

47

N-(6-(trifluoromethyl)thiazolo[4,5-c]pyridin-2-yl)
pyridazine-4-carboxamide

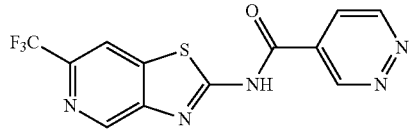 [SMILES: O=C(Nc1nc2cnc(C(F)(F)F)cc2s1)c1ccncn1]

$^1$H NMR (400 MHz, DMSO): 13.83 (s, 1H), 9.76 (dd, J=2.32, 1.26 Hz, 1H), 9.57 (dd, J=5.31, 1.22 Hz, 1H), 9.23 (s, 1H), 8.77 (s, 1H), 8.28 (dd, J=5.32, 2.37 Hz, 1H). [M+1]$^+$=326.1

N-(6-(trifluoromethyl)thiazolo[4,5-c]pyridin-2-yl)
pyrimidine-4-carboxamide

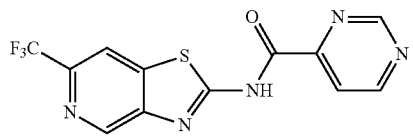

$^1$H NMR (400 MHz, DMSO): 13.38 (s, 1H), 9.51 (d, J=1.41 Hz, 1H), 9.25 (s, 1H), 9.22 (d, J=5.12 Hz, 1H), 8.80 (s, 1H), 8.24 (dd, J=5.11, 1.26 Hz, 1H). [M+1]$^+$=326.1

N-(6-(trifluoromethyl)thiazolo[4,5-c]pyridin-2-yl)
thiazole-5-carboxamide

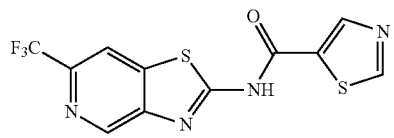 [SMILES: O=C(Nc1nc2cnc(C(F)(F)F)cc2s1)c1cncs1]

$^1$H NMR (400 MHz, DMSO): 13.68 (s, 1H), 9.63 (s, 1H), 9.56 (s, 1H), 9.44 (s, 1H), 9.04 (s, 1H). [M+1]$^+$=331.0

N-(6-methoxythiazolo[4,5-c]pyridin-2-yl)benzamide

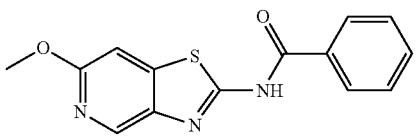 [SMILES: COc1cc2sc(NC(=O)c3ccccc3)nc2cn1]

$^1$H NMR (400 MHz, Acetone): 8.59 (s, 1H), 8.23 (s, 1H), 8.21 (t, J=1.57 Hz, 1H), 7.70 (t, J=7.37 Hz, 1H), 7.61 (t, J=7.59 Hz, 2H), 7.36 (s, 1H), 3.95 (s, 3H). [M+1]$^+$=286.1

48

N-(6-(trifluoromethyl)thiazolo[4,5-c]pyridin-2-yl)-
1H-pyrazole-3-carboxamide

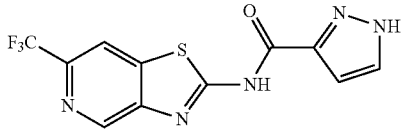 [SMILES: O=C(Nc1nc2cnc(C(F)(F)F)cc2s1)c1cc[nH]n1]

$^1$H NMR (400 MHz, acetone): 9.09 (s, 1H), 8.59 (s, 1H), 8.00 (s, 1H), 7.05 (s, 1H). [M+1]$^+$=314.1

N-(6-(trifluoromethyl)thiazolo[4,5-c]pyridin-2-yl)
isoxazole-5-carboxamide

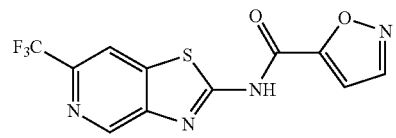 [SMILES: O=C(Nc1nc2cnc(C(F)(F)F)cc2s1)c1ccno1]

$^1$H NMR (400 MHz, acetone): 9.143 (s, 1H), 8.762 (d, J=1.92 Hz, 1H), 8.635 (s, 1H), 7.505 (d, J=1.92 Hz, 1H). [M+1]$^+$=315.1

5-methyl-N-(6-(trifluoromethyl)thiazolo[4,5-c]pyridin-2-yl)isoxazole-3-carboxamide

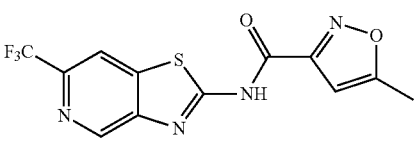 [SMILES: Cc1cc(C(=O)Nc2nc3cnc(C(F)(F)F)cc3s2)no1]

$^1$H NMR (400 MHz, DMSO): 13.69 (s, 1H), 9.21 (s, 1H), 8.76 (s, 1H), 6.89 (s, 1H), 2.54 (s, 3H). [M+1]$^+$=329.1

N-(6-(trifluoromethyl)thiazolo[4,5-c]pyridin-2-yl)
isothiazole-5-carboxamide

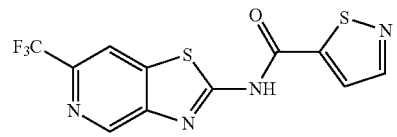

$^1$H NMR (400 MHz, DMSO): 13.82 (s, 1H), 9.20 (s, 1H), 8.81 (d, J=1.88 Hz, 1H), 8.75 (s, 1H), 8.37 (d, J=1.81, 1H). [M+1]$^+$=331.1

N-(6-(trifluoromethyl)thiazolo[4,5-c]pyridin-2-yl)
isothiazole-4-carboxamide

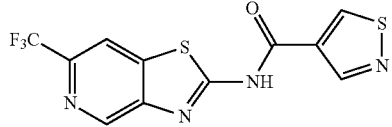 [SMILES: O=C(Nc1nc2cnc(C(F)(F)F)cc2s1)c1cnsc1]

¹H NMR (400 MHz, DMSO): 13.46 (s, 1H), 10.05 (s, 1H), 9.18 (s, 2H), 8.74 (s, 1H). [M+1]⁺=331.0

N-(6-(trifluoromethyl)thiazolo[4,5-c]pyridin-2-yl)
isothiazole-3-carboxamide

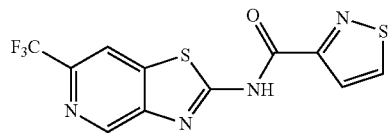 [SMILES: O=C(Nc1nc2cnc(C(F)(F)F)cc2s1)c1ccsn1]

¹H NMR (400 MHz, DMSO): 13.42 (s, 1H), 9.29 (d, J=4.72 Hz, 1H), 9.20 (s, 1H), 8.75 (s, 1H), 8.07 (d, J=4.7, 1H). [M+1]⁺=331.1

N-(6-(trifluoromethyl)oxazolo[4,5-c]pyridin-2-yl)
benzamide

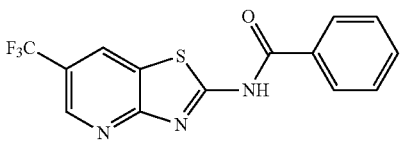

¹H NMR (400 MHz, DMSO): 8.97 (s, 1H), 8.34 (s, 1H), 8.05 (d, J=7.35 Hz, 2H), 7.56-7.53 (m, 3H). [M+1]⁺=308.1

N-(6-(trifluoromethyl)thiazolo[4,5-b]pyridin-2-yl)
benzamide

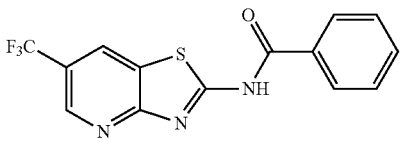

¹H NMR (500 MHz, DMSO): 13.46 (s, 1H), 9.01 (s, 1H), 8.94 (s, 1H), 8.18 (d, J=7.31 Hz, 2H), 7.71 (t, J=7.38 Hz, 1H), 7.60 (t, J=7.71 Hz, 2H). [M+1]⁺=324.1

N-(6-(trifluoromethyl)thiazolo[4,5-b]pyridin-2-yl)
picolinamide

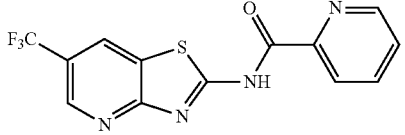

¹H NMR (500 MHz, DMSO): 9.03 (d, J=1.87 Hz, 1H), 8.95 (t, J=1.13 Hz, 1H), 8.82 (ddd, J=4.70, 1.58, 0.90 Hz, 1H), 8.24 (dt, J=7.81, 0.98 Hz, 1H), 8.14 (td, J=7.71, 1.68 Hz, 1H), 7.78 (ddd, J=7.58, 4.73, 1.18 Hz, 1H). [M+1]⁺=325.1

N-(6-(trifluoromethyl)thiazolo[4,5-b]pyridin-2-yl)
thiazole-4-carboxamide

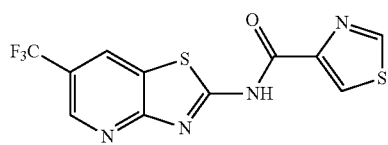 [SMILES: O=C(Nc1nc2ncc(C(F)(F)F)cc2s1)c1cscn1]

¹H NMR (500 MHz, DMSO): 9.06 (s, 1H), 8.55 (s, 1H), 8.38 (s, 1H), 8.31 (s, 1H). [M+1]⁺=331.0

N-(6-(trifluoromethyl)thiazolo[4,5-b]pyridin-2-yl)
thiazole-5-carboxamide

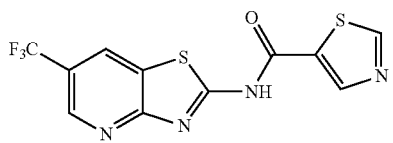 [SMILES: O=C(Nc1nc2ncc(C(F)(F)F)cc2s1)c1cncs1]

¹H NMR (500 MHz, DMSO): 9.43 (s, 1H), 8.95 (d, J=7.20 Hz, 2H), 8.91 (s, 1H). [M+1]⁺=331.0

N-(6-trifluoromethyl)thiazolo[4,5-c]pyridin-2-yl)
oxazole-2-carboxamide

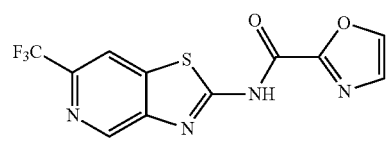 [SMILES: O=C(Nc1nc2cnc(C(F)(F)F)cc2s1)c1ncco1]

¹H NMR (400 MHz, Acetone): 9.10 (s, 1H), 8.58 (br, 1H), 8.33 (d, J=1.0 Hz, 1H), 7.55 (br, 1H). [M+1]⁺=315.0

What is claimed is:

1. A compound having the formula of formula II:

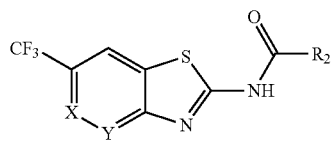

wherein X is selected from the group consisting of carbon or nitrogen;

Y is selected from the group consisting of carbon or nitrogen;

R₂ is selected from unsubstituted or substituted phenyl, unsubstituted or substituted heteroaryl, wherein the unsubstituted heteroaryl is selected from the group consisting of a 6-membered heteroaryl and a 5-membered heteroaryl, and wherein when R₂ is a substituted phenyl or substituted heteroaryl, the substitution is selected from the group consisting of hydrogen, halogen, lower alkyl and combinations thereof; and wherein at least one of X or Y is nitrogen.

2. The compound as set forth in claim 1, wherein R₂ is selected from:

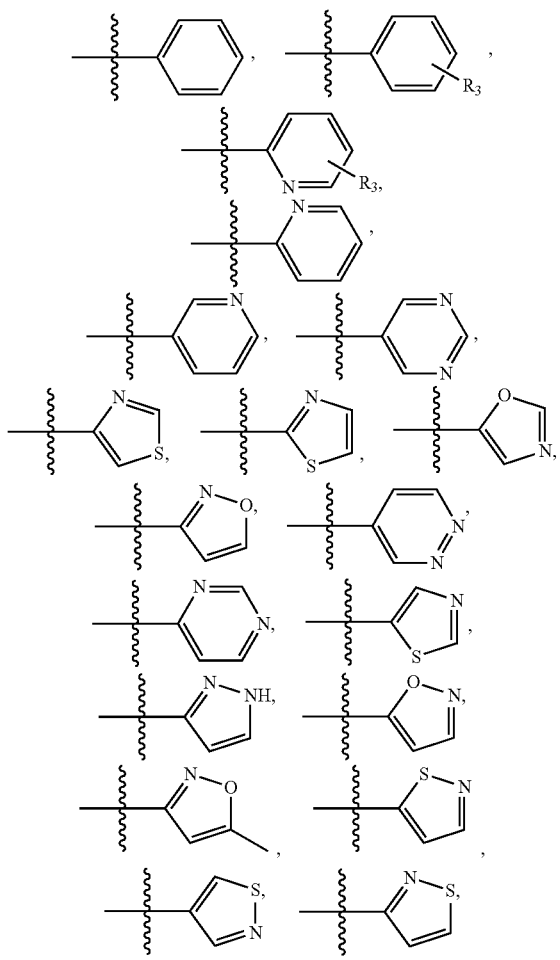

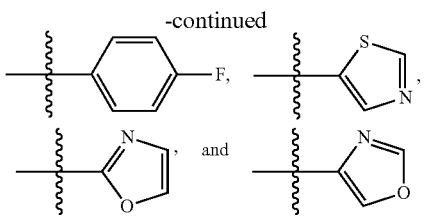

wherein R₃ is selected from lower alkyl, and halogen.

3. The compound as set forth in claim 1 selected from the group consisting of:

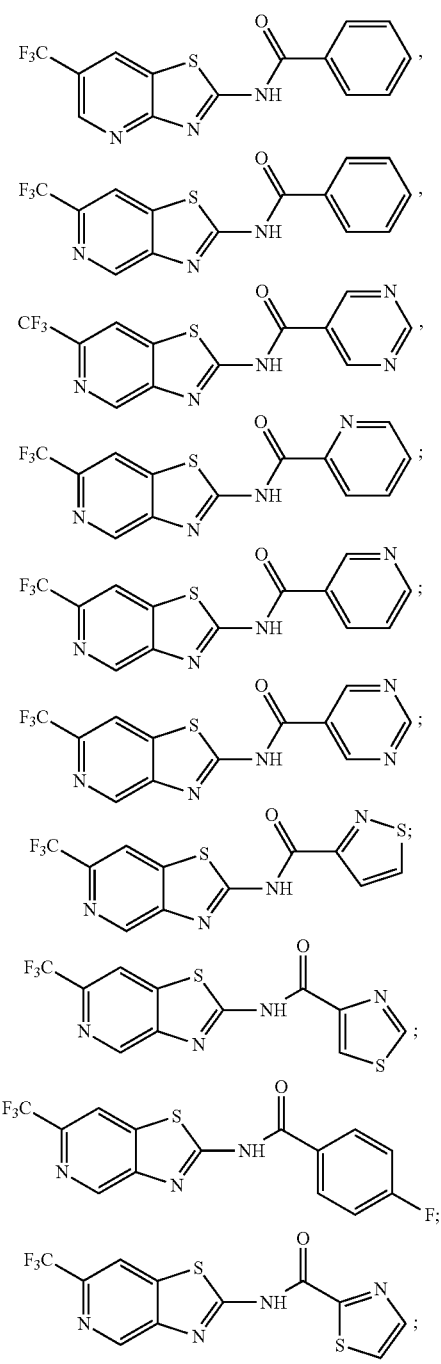

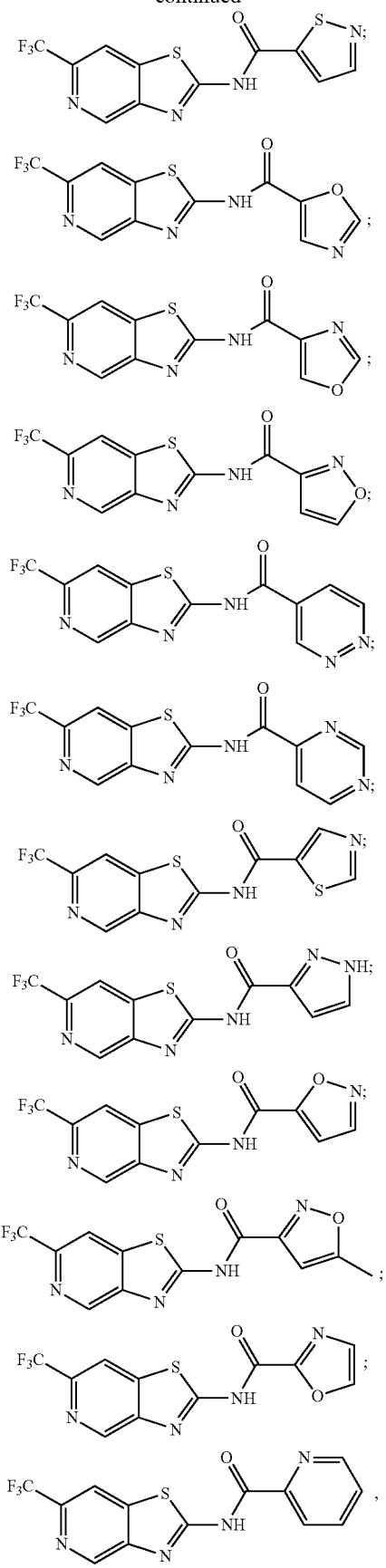
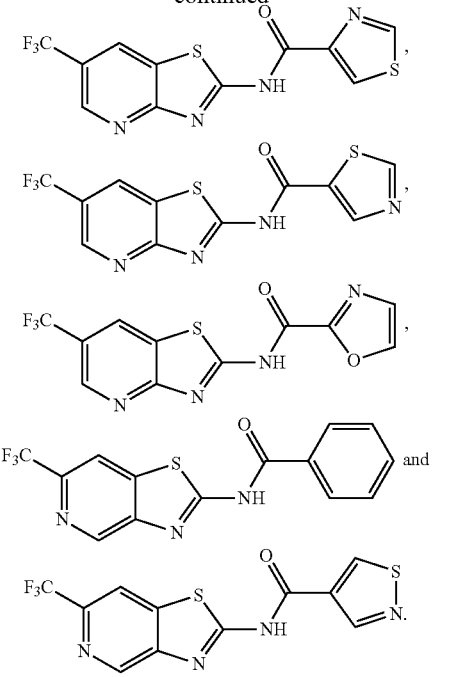
4. The compound as set forth in claim 1 comprising
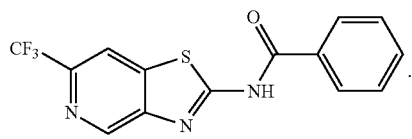
5. A composition comprising the compound as set forth in claim 1 and a pharmaceutically acceptable carrier, adjuvant or vehicle.
6. The composition as set forth in claim 5, wherein $R_2$ is selected from:
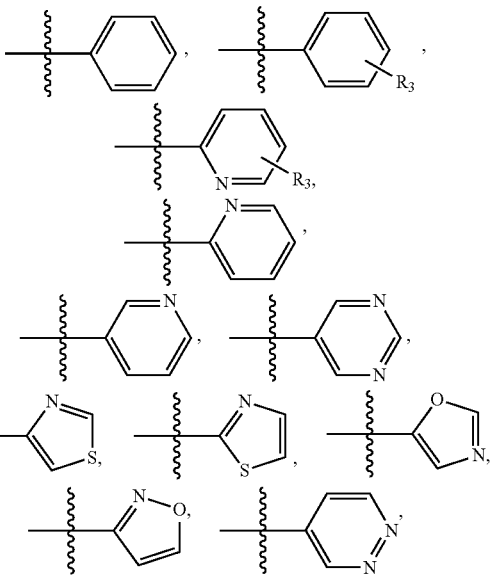

-continued
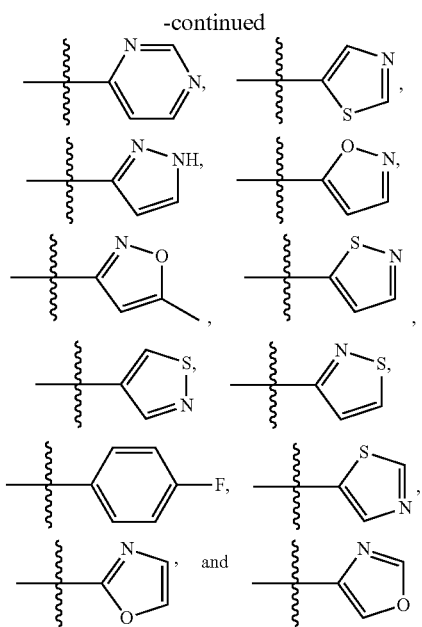
wherein R₃ is selected from lower alkyl, and halogen.
7. The composition as set forth in claim 5, wherein the compound is selected from the group consisting of:
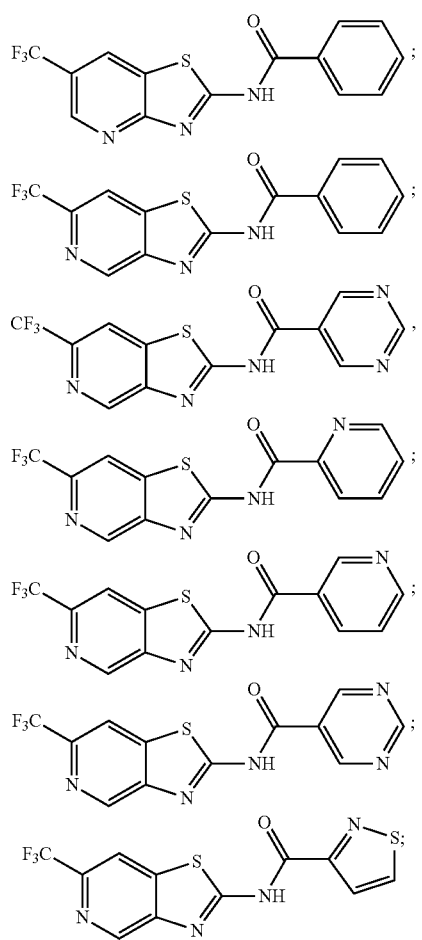
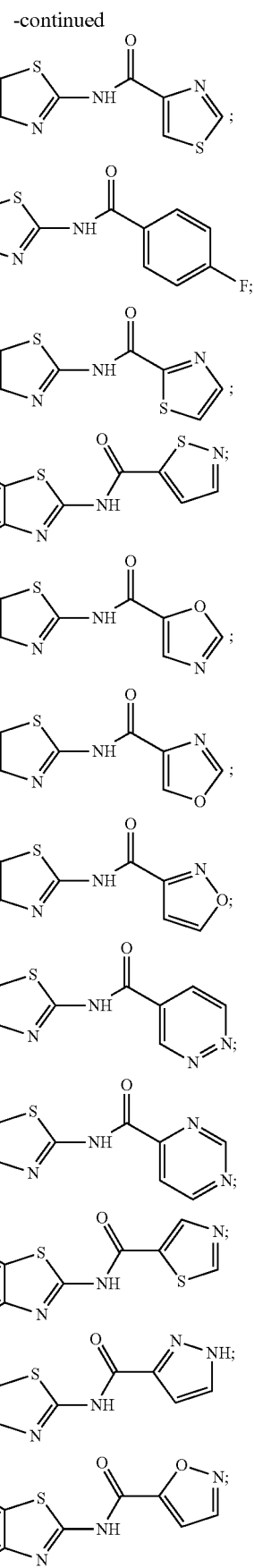

-continued

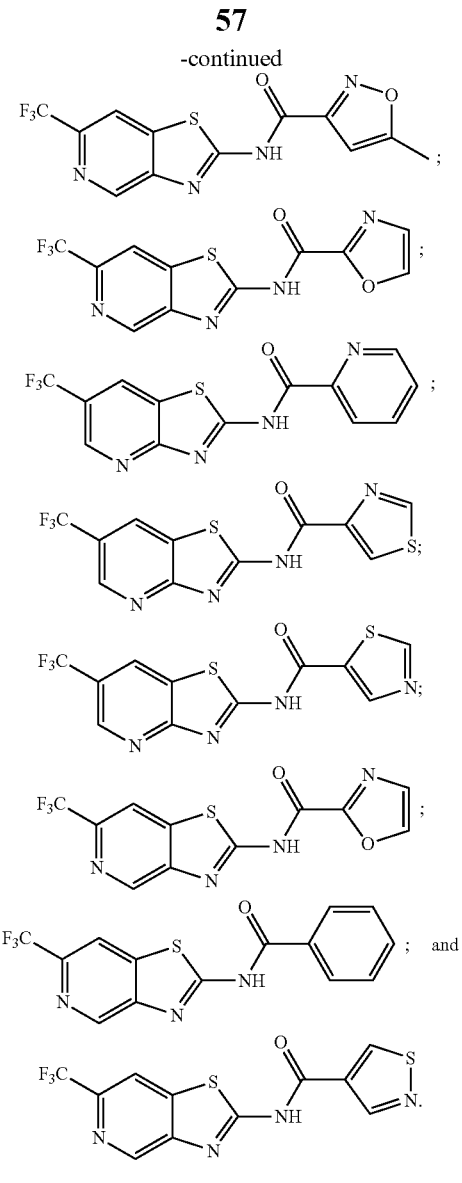

8. The composition as set forth in claim 5, wherein the compound is

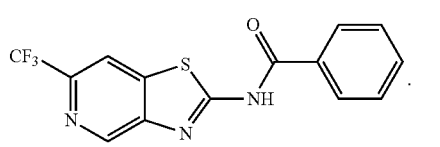

9. A method of treating spinal muscular atrophy in a subject in need thereof, the method comprising administering the compound as set forth in claim 1.

10. The method as set forth in claim 9, wherein $R_2$ is selected from:

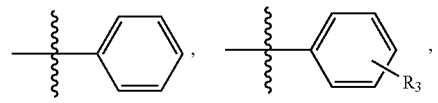

-continued

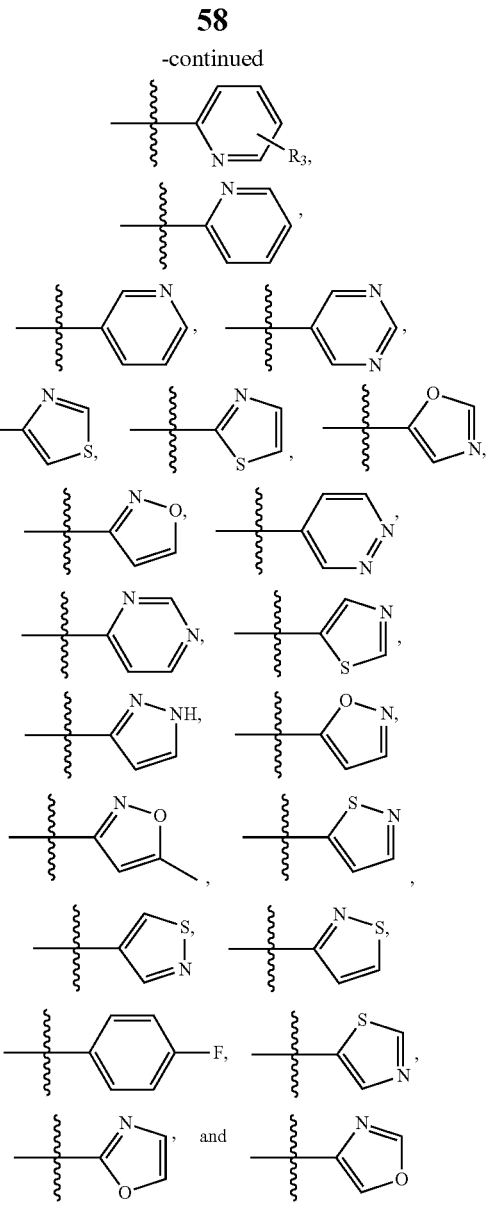

wherein $R_3$ is selected from lower alkyl and halogen.

11. The method as set forth in claim 9, wherein the compound is selected from the group consisting of:

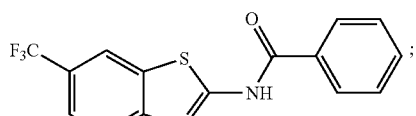

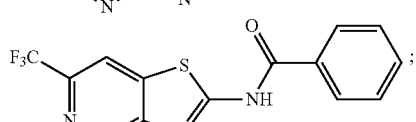

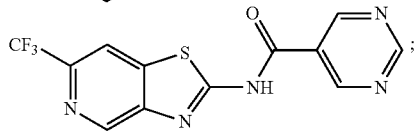

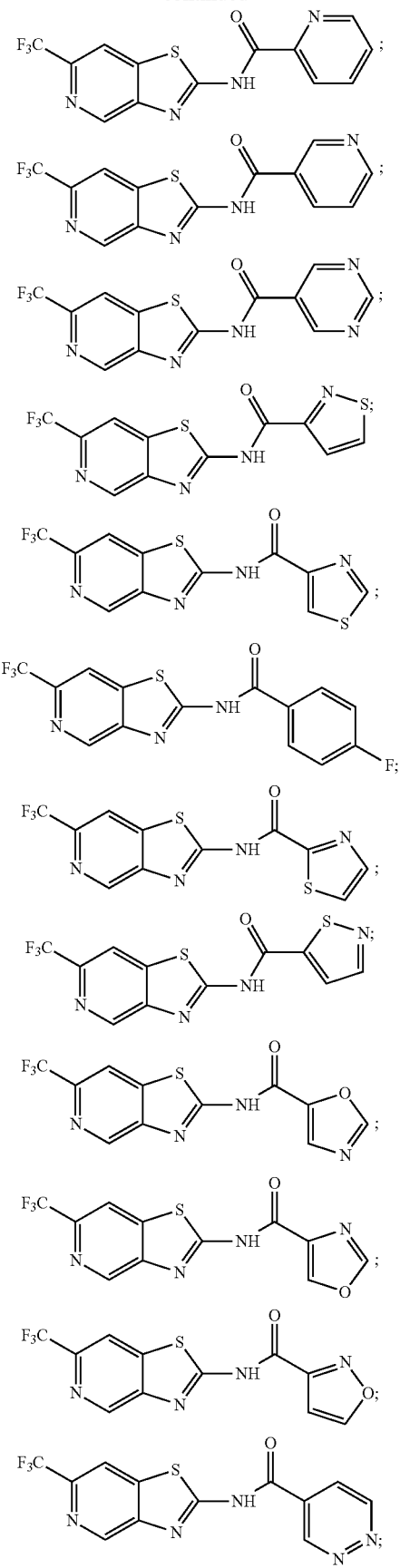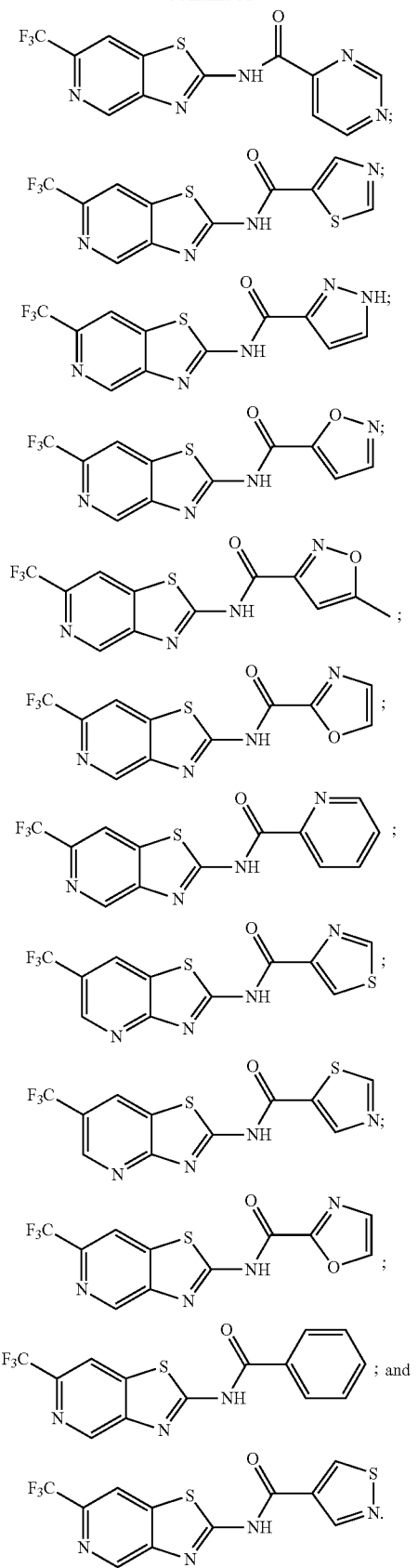

12. The method as set forth in claim 9, wherein the compound is

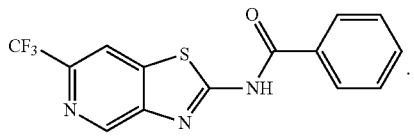 [SMILES: O=C(Nc1nc2cnc(C(F)(F)F)cc2s1)c1ccccc1]

13. The method as set forth in claim 9, wherein the compound is administered by a method selected from the group consisting of orally, subcanteously, and intraperitoneally.

14. A method of treating spinal muscular atrophy in a subject in need thereof, the method comprising administering a SMN gene replacement therapy and a compound as set forth in claim 1.

15. The method as set forth in claim 14, wherein R₂ is selected from:

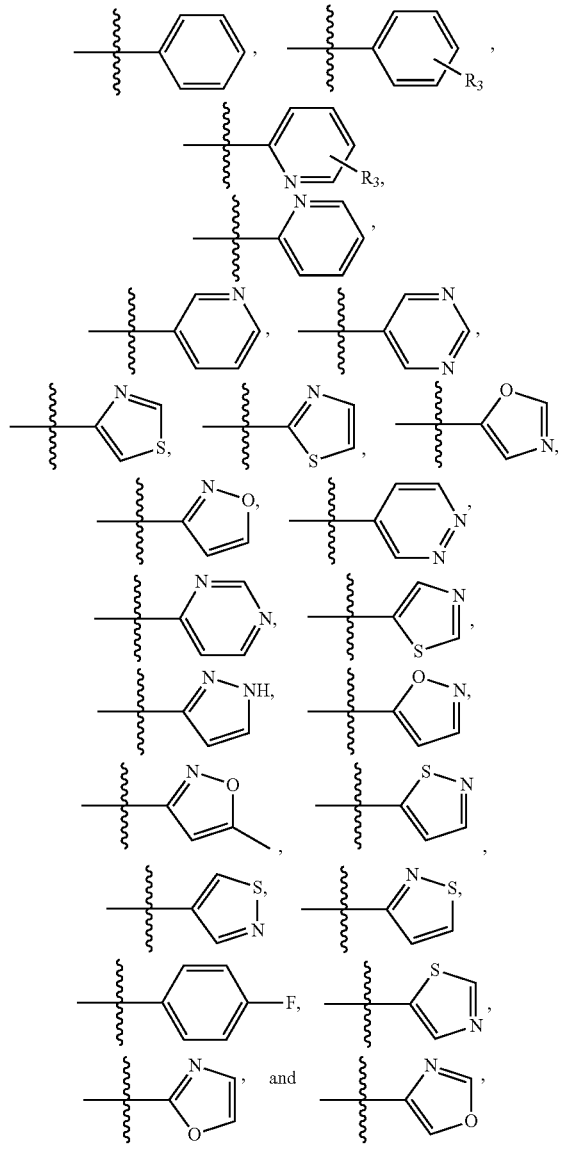

wherein R₃ is selected from lower alkyl and halogen.

16. The method as set forth in claim 14, wherein the compound is selected from the group consisting of:

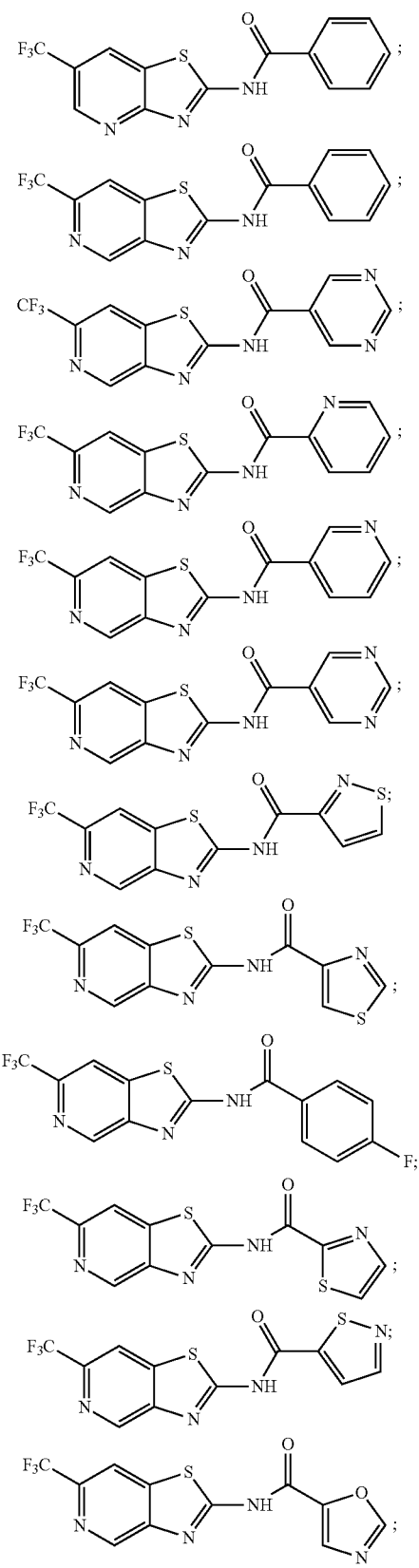

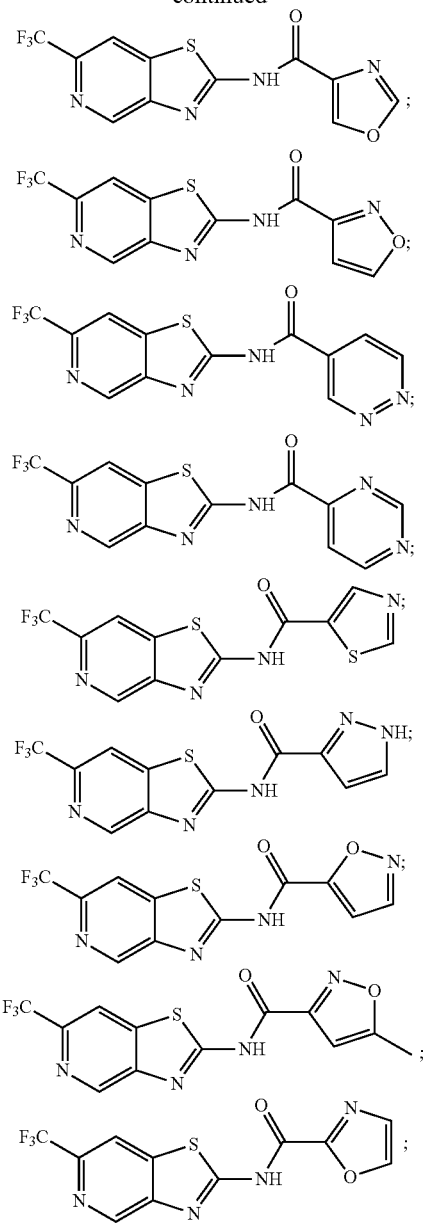
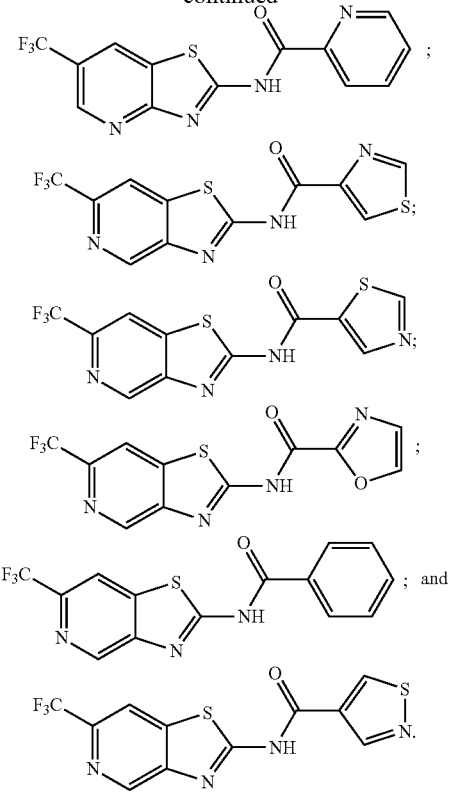
17. The method as set forth in claim 1, wherein the compound is
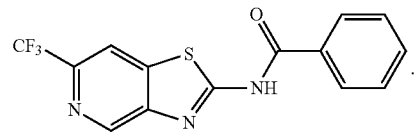 [SMILES: O=C(Nc1nc2cnc(C(F)(F)F)cc2s1)c1ccccc1]
18. The method as set forth in claim 14, wherein the compound is administered by a method selected from the group consisting of orally, subcanteously, and intraperitoneally.
* * * * *